United States Patent [19]
Levinson et al.

[11] Patent Number: 6,146,827
[45] Date of Patent: Nov. 14, 2000

[54] RATH GENES AND POLYPEPTIDES AND METHODS FOR THE TREATMENT AND DIAGNOSIS OF IMMUNE DISORDERS

[75] Inventors: Douglas Adam Levinson, Sherborn; Carlos J. Gimeno, Boston, both of Mass.

[73] Assignee: Millennium Pharmaceuticals, Inc., Cambridge, Mass.

[21] Appl. No.: 08/949,004

[22] Filed: Oct. 10, 1997

Related U.S. Application Data

[60] Division of application No. 08/870,815, Jun. 6, 1997, Pat. No. 6,020,142, which is a continuation-in-part of application No. 08/726,228, Oct. 4, 1996, Pat. No. 5,846,780.

[51] Int. Cl.⁷ .............................. C12Q 1/68; C12N 15/85; C12N 15/11; C07H 21/04
[52] U.S. Cl. .......................... 435/6; 435/69.1; 435/320.1; 435/355; 435/366; 435/372.3; 536/23.1; 536/23.5; 536/24.3; 536/24.31; 536/24.33
[58] Field of Search ................................ 435/69.1, 172.3, 435/320.1, 355, 6, 366, 372.3, 440; 536/24.31, 23.1, 24.3, 23.5, 24.33; 530/387.1

[56] References Cited

U.S. PATENT DOCUMENTS

| | | | |
|---|---|---|---|
| 5,073,627 | 12/1991 | Curtis et al. | 530/351 |
| 5,514,546 | 5/1996 | Kool | 435/6 |
| 5,585,478 | 12/1996 | Lim et al. | 536/23.5 |
| 5,667,987 | 9/1997 | Buckbinder et al. | 435/69.1 |
| 5,871,961 | 2/1999 | Smith et al. | 435/69.1 |

FOREIGN PATENT DOCUMENTS

| | | |
|---|---|---|
| WO 96/01907 | 1/1996 | WIPO . |
| WO 96/39427 | 6/1996 | WIPO . |

OTHER PUBLICATIONS

Siderovski et al. DNA and Cell Biology. vol. 9. pp. 579–587. (1990).
Meinkoth et al. Analytical Biochemistry. vol. 138, 267–285 (1984).
Liu et al. Biotechniques. V. 18. pp. 470–477 (1995).
Doolittle, Of URFS and ORFS, A Primer on How to Analyze Derived Amino Acid Sequences, University Science Books, Mill Valley CA (1986).
Assadi and Greer, 1996, "Site–Ordering Effects on Element Partitioning During Rapid Solidification of Alloys", Nature 383:150–152.
Bacon, K. et al., 1995, "IL–8–Induced Signal Transduction in T Lymphocytes Involves Receptor–Mediated Activation of Phospholipases C and D", J. Immunology 154:3654–3666.
Berman, D. et al., 1996, "GAIP and RGS4 are GTPase–Activating Proteins for the $G_i$ Subfamily of G Protein α Subunits", Cell 86:445–452.
Brunelli and Pall, 1993, "A Series of Yeast Shuttle Vectors for Expression of cDNAs and Other DNA Sequences", Yeast 9:1299–1308.

Damaj, B. et al., 1996, "Physical Association of $G_{i2\alpha}$ with Interleukin–8 Receptors", J. Biol. Chem. 271:12783–12789.
Del Prete, G. et al., 1991, "Purified Protein Derivative of *Mycobacterium tuberculosis* and Excretory–Secretory Antigen(s) of *Toxocara canis* Expand In Vitro Human T Cells with Stable and Opposite (Type 1 T Helper or Type 2 T Helper) Profile of Cytokine Production", J. Clin. Invest. 88:346–350.
De Vries, L. et al., 1995, "GAIP, a Protein that Specifically Interacts with the Trimeric G Protein $G\alpha_{i3}$, is a Member of a Protein Family with a Highly Conserved Core Domain", PNAS USA 92:11916–11920.
Dietzel and Kurjan, 1987, "Pheromonal Regulation and Sequence of the *Saccharomyces cerevisiae* SST2 Gene: a Model for Desensitization to Pheromone", Mol. Cell. Biol. 7:4169–4177.
Dohlman, H. et al., 1995, "Inhibition of G–Protein Signaling by Dominant Gain–of–Function Mutations in Sst2p, a Pheromone Desensitization Factor in *Saccharomyces cerevisiae*", Mol. Cell. Biol. 15:3635–3643.
Druey, K. et al., 1996, "Inhibition of G–Protein–Mediated MAP Kinase Activation by a New Mammalian Gene Family", Nature 379:742–746.
Eason, M. et al., 1996, "Chimeric–Mutagenesis of Putative G–Protein Coupling Domains of the $a_{2a}$–Adrenergic Receptor", J. Biol. Chem. 271:12826–12832.
Ebtekar and Khansari, 1996, "Differential Antigenic Stimulation Influences Cytokine Production Patterns in T Cells and CD4⁺ Subpopulations" Scand. J. Immunol. 43:391–397.
Farrar, M. et al., 1996, "Activation of the Raf–1 Kinase Cascade by Coumermycin–induced Dimerization", Nature 383:178–181.
Firestein, G. et al., 1989, "A New Murine CD4³⁰ T Cell Subset with an Unrestricted Cytoknie Profile", J. Immunol. 143:518–525.
Franklin, R. et al., 1993, "Platelet–Activating Factor Triggers the Phosphorylation and Activation of MAP–2 Kinase and S6 Peptide Kinase Activity in Human B Cell Lines", J. Immunology 151:1802–1810.

(List continued on next page.)

*Primary Examiner*—George C. Elliott
*Assistant Examiner*—Mark L. Shibuya
*Attorney, Agent, or Firm*—Pennie & Edmonds LLP

[57] ABSTRACT

The present invention relates, first, to the identification of novel nucleic acid molecules, termed RATH genes and RATH gene products encoded by such nucleic acid molecules, or degenerate variants thereof, that participate in the regulation, control and/or modulation of G-protein-mediated signal transduction involved in T cell activation, including, but not limited to T helper (TH) cell and TH cell subpopulation activation. Specifically, the nucleic acid molecules of the present invention include the genes corresponding to the mammalian RATH genes, including the RATH1.1 genes. Sequence analysis indicates that the RATH genes are novel genes belonging to the RGS ("regulator of G-protein signalling") gene family, a gene family which encodes gene products involved in G-protein-mediated signal transduction.

16 Claims, 5 Drawing Sheets

OTHER PUBLICATIONS

Garland, A.M. et al., 1996, "Mechanisms of Desensitization and Resensitization of G Protein–Coupled Neurokinin$_1$ and Neurokinin$_2$ Receptors", Mol. Pharmacol. 49:438–446.

Hunt, T. et al., 1996, "RGS10 is a Selective Activator of G$\alpha_i$ GTPase Activity", Nature 383:175–177.

Kaziro, Y. et al., 1991, "Structure and Function of Signal–Transducing GTP–Binding Proteins", Annual Rev. Biochem. 60:363–373.

Koelle and Horvitz, 1996, "EGL–10 Regulates G Protein Signaling in the C elegans Nervous System and Shares a Conserved Domain with Many Mammalian Proteins", Cell 84:115–125.

Kuang, Y. et al., 1996, "Selective G Protein Coupling by C–C Chemokine Receptors", J. Biol. Chem. 271:3975–3978.

Kurjan, J., 1993, "The Pheromone Response Pathway in *Saccharomyces cerevisiae*", Annu. Rev. Genet. 27:147–179.

Liu and Simon, 1996, "Regulation by cAMP–dependent Protein Kinase of a G–Protein–Mediated Phospholipase C", Nature 382:83–87.

Luo, Z. et al., 1996, "Oligomerization Activates c–Raf–1 through a Ras–Dependent Mechanism", Nature 383:181–185.

Machesky and Hall, 1996, "Rho: A Connection between Membrane Receptor Signalling and the Cycoskeleton", Trends in Cell Biol. 6:304–310.

Maggi, E. et al., 1994, "Th2–like CD8$^+$ T Cells Shoeing B Cell Helper Function and Reduced Cytolytic Activity in Human Immunodeficiency Virus Type 1 Infection", J. Exp. Med. 180:489–495.

Manetti, R, et al., 1994, "CD30 Expression by CD8$^+$ T Cells Producing Type 2 Helper Cytokines. Evidence for Large Numbers of CD8$^+$CD30$^+$ T Cell Clones in Human Immunodeficiency Virus Infection", J. Exp. Med. 180:2407–2411.

McKean, D. et al., 1994, "Ligand–induced Desensitization of Interleukin 1 Receptor–initiated Intracellular Signaling Events in T Helper Lymphocytes", J. Exp. Med. 180:1321–1328.

Moorman, J. et al., 1996, "Inactivation of the small GTP Binding Protein Rho Induces Multinucleate Cell Formation and Apoptosis in Murine T Lymphoma EL4$^{1,2}$", J. Immunol. 156:4146–4153.

Mosmann and Coffman, 1989, "TH1 and TH2 Cells: Different Patterns of Lymphokine Secretion Lead to Different Functional Properties", Ann. Rev. Immunol. 7:145–173.

Murphy and Tiffany, 1991, "Cloning of Complementary DNA Encoding a Functinoal Human Interleukin-8 Receptor", Science 253:1280–1283.

Murphy, P., 1994, "The Molecular Biology fo Leukocyte Chemoattractant Receptors", Annu. Rev. Immunol. 12:593–633.

Newton, J. et al., 1993, "A B Cell Specific Immediate Early Human Gene is Located on Chromosome Band 1q31 and Encodes an $\alpha$ Helical Basic Phosphoprotein", Biochimica et Biophysica Acta 1216:314–316.

Nuoffer and Balch, 1994, "GTPases: Multifunctional Molecular Switches Regulating Vesicular Traffic", Annu. Rev. Biochem. 63:949–990.

Oppermann, M. et al., 1996, "Phosphorylation of the Type 1A Angiotensin II Receptor by G Protein–coupled Receptors Kinases and Protein Kinase C", J. Biol. Chem. 271:13266–13272.

Robinson, D. et al., 1993, Activation of CD4+ T Cells, Increased T$_{H2}$–type Cytokine mRNA Expression, and Eosinophil Recruitment in Bronchoalveolar Lavage after Allergen Inhalation Challenge.

Roush, W., 1996, "Regulating G Protein Signaling", Science 271:1056–1058.

Safko, M. et al., 1981, "Heterologous Desensitization of Leukocytes: A Possible Mechanism of Beta Adrenergic Blockade in Atopic Dermatitis", J. Allergy Clin. Immunol. 68:218–225.

Schall, T. et al., 1990, "Selective Attraction of Monocytes and T Lymphocytes of the Memory Phenotype by Cytokine Rantes", Nature 347:669–671.

Schreurs, J. et al., 1984, "Pharmacological Characterization of Histamine H$_2$ Receptors on Clonal Cytolic T Lymphocytes", Biochemical Pharmacology 33:3375–3382.

Seder and Gros, 1995, "The Functional Role of CD8$^+$ T Helper Type 2 Cells", J. Exp. Med. 181:5–7.

Siderovski, D. et al., 1996, "A New Family of Regulators of G–protein–coupled Receptors?", Curr. Biol. 6:211–212.

Soloman, K. et al., 1996, "The Association Between Glycosylphosphatidylinositol–anchored Proteins and Heterotrimeric G Protein a Subunits in Lymphocytes", PNAS USA 93:6053–6058.

Tomhave, E, et al., 1994, "Cross–Desensitization of Receptors for Peptide Chemoattractants", J. Immunol. 153:3267–3275.

Torres and Ye, 1996, "Activation of the Mitogen–activated Protein Kinase Pathway by fMet–Leu–Phe in the Absence of Lyn and Tyrosine Phosphorylation of SHC in Transfected Cells", J. Biol. Chem. 271:13244–13249.

Watson, N et al., 1996, "RGS Family Members: GTPase–activating Proteins for heterotrimeric G–protein Alpha– subunits", Nature 383:172–175.

Weiner, J. et al., 1993, "Disruption of Receptor–G Protein Coupling in Yeast Promotes the Function of an SST2–dependent Adaptation Pathway", J. Biol. Chem. 268:8070–8077.

Wierenga, E. et al., 1990, "Evidence for Compartmentalization of Functional Subsets of CD4$^+$ T Lymphocytes in Atopic Patients", J. Immunol. 144:4651–4656.

Wilson, R. et al., 1994, "2.2Mb of Contiguous Nucleotide Sequence from Chromosome III of *C. elegans*", Nature 368:32–38.

Wilson, M. et al., 1996, "Wortmannin–sensitive Activation of p70$^{s6k}$ by Endogenous and Heterologously Expressed G$_1$–coupled Receptors", J. Biol. Chem. 271:8537–8540.

Yamamura, M. et al., 1991, "Defining Protective Responses to Pathogens: Cytokine Profiles in Leprosy Lesions", Science 254:277–279.

Zhang, Y. t al., 1996, "Receptor–associated Mad Homologues Synergize as Effectors of the TGF–$\beta$ Response", Nature 383:168–172.

Albelda and Buck, 1990, "Integrins and Other Cell Adhesion Molecules", FASEB Journal 4:2868–2880.

Bazzoni, G. et al., 1996 "Bcr/Abl Expression Stimulates Integrin Function in Hematopoietic Cell Lines", Bcr/Abl and Integrin Function 98:521–528.

Bhatia, R. et al., 1994, "Interferon–$\alpha$ Restores Normal Adhesion of Chronic Myelogenous Leukemia Hematopoietic Progenitors to Bone Marrow Stroma by Correcting Impaired $\beta$1 Integrin Receptor Function", J. Clin. Invest. 94:384–391.

Chasserot–Golaz, S. et al., 1996, "Annexin II in Exocytosis: Catecholamine Secretion Requires the Translocation of p36 to the Subplamalemmal Region in Chromaffin Cells", J. Cell Biol. 133:1217–1236.

Cifone, M. et al., 1996, "Phospholipase $A_2$ Activity and Calpactin I Levels in Rat Lymphokine–Activated Killer Cells: Correlation with the Cytotoxic Activity", Cell. Immunology 170:274–282.

Damle and Aruffo, 1991, "Vascular Cell Adhesion Molecule 1 Induces T–cell Antigen Receptor–Dependent Activation of $CD4^+$ T Lymphocytes", PNAS 88:6403–6407.

Dubois, T. et al., 1995, "In Vivo and In Vitro Phosphorylation of Annexin II in T Cells: Potential Regulation by Annexin V", Biochem. J. 310:243–248.

Emans N et al. 1993 "Annexin II Is a Major Component of Eusogenic Endosomal Vesicles" J. Cell.

Figdor, C. et al., 1990, "On the Mode of Action", Immunology Today 11:277–280.

Gumbiner, B., 1993, "Proteins Associated with the Cytoplasmic Surface of Adhesion Molecules", Neuron 11:551–564.

Hogg, N. et al., 1992, "Leukocyte Integrin Activation", Kidney International 41:613–616.

Jesaitis, A.J. et al., 1993, "Functional Molecular Complexes of Human N–Formyl Chemoattractant Receptors and Actin", J. Immunol. 151:5653–5665.

Jesaitis, A.J. et al., 1993, "Cytoskeletal Regulation of Chemotactic Receptors: Molecular Complexation of N–formyl Peptide Receptors with G Proteins and Actin", Eur. J. Haematol. 51:288–293.

Jones, S. et al., 1995, "A Comparison of Post–Receptor Signal Transduction Events in Jurkat Cells Transfected with either IL–8R1 or IL–8R2 Chemokine Mediated Activation of p42/p44 MAP–kinase (ERK–2)", FEBS Letters 364:211–214.

Masumoto and Hemler, 1993, "Multiple Activation States of VLA–4", J. Biol. Chem. 268:228–234.

Schwartz–Albiez, R. et al., 1993, "Differential Expression of Annexins I and II in Normal and Malignant Human Mammary Epithelial Cells", Differentiation 52:229–237.

Tressler, R. et al., 1993, "Extracellular Annexin II is Associated with Divalent Cation–Dependent Tumor Cell–Endothelial Cell Adhesion of Metastatic RAW117 Large–Cell Lymphoma Cells", J. Cell. Biochem. 53:265–276.

Vuillet–Gaugler, M.H. et al., 1990, "Loss of Attachment to Fibronectin with Terminal Human Erythroid Differentiation", Blood 75:865–873.

Waisman, D., 1995, "Annexin II Tetramer: Structure and Function", Mol. and Cell. Biochem. 149/150:301–322.

Whitehurst and Geppert, 1996, "MEK1 and the Extracellular Signal–Regulated Kinases are Required for the Stimulation of IL–2 Gene Transcription in T Cells", J. Immunol. 156:1020–1029.

Popov et al., 1997, "The regulators of G protein signaling (RGS) domains of RGS4, RGS10, and GAIP retain GTPase activating protein activity in vitro", PNAS USA 94:7216–7220.

```
                                    M   C   R   T   L   A   T   F   P       9
CCACGGCGTCCGGCCACGACGTGCTGCTGCCTGCGTCCGGCAACC ATG TGC CGC ACC CTA GCC ACC TTC CCC    27

N   T   C   L   E   R   A   K   E   F   K   T   R   L   G   I   F   L   H   K     29
AAC ACC TGC CTG GAG AGA GCC AAA GAG TTC AAG ACG CGG CTG GGA ATC TTT CTT CAT AAA    87

S   E   L   S   S   D   T   G   G   I   S   K   F   E   W   A   S   K   H   N     49
TCA GAG CTG AGC TCC GAT ACT GGG GGT ATT AGC AAA TTC GAG TGG GCC AGT AAG CAT AAC    147

K   E   R   S   F   S   E   D   V   L   G   W   R   E   S   F   D   L   L   L     69
AAA GAG AGA AGC TTC TCA GAA GAT GTA CTG GGA TGG AGA GAG TCT TTC GAT TTG CTG CTG    207

N   S   K   N   G   V   A   A   F   H   A   F   L   K   T   E   F   S   E   E     89
AAC AGT AAA AAT GGG GTG GCT GCC TTC CAT GCC TTC CTA AAG ACG GAA TTC AGT GAG GAG    267

N   L   E   F   W   L   A   C   E   E   F   K   K   I   R   S   A   T   K   L    109
AAC CTG GAG TTC TGG TTG GCC TGC GAG GAG TTC AAG AAG ATC CGA TCA GCC ACC AAA CTG    327

A   S   R   A   H   H   I   F   D   E   Y   I   R   S   E   A   P   K   E   V    129
GCG TCC AGG GCT CAC CAC ATC TTT GAC GAG TAC ATC CGC AGC GAA GCC CCT AAA GAG GTG    387

N   I   D   H   E   T   R   E   L   T   K   T   N   L   Q   A   A   T   S        149
AAC ATA GAT CAC GAG ACC CGA GAA CTG ACC AAG ACA AAC CTA CAA GCT GCC ACT AGT        447

C   F   D   V   A   Q   G   K   T   R   T   L   M   E   K   D   S   Y   P   R    169
TGC TTC GAT GTG GCT CAG GGG AAG ACC CGC ACA TTG ATG GAG AAG GAC TCC TAT CCG CGC    507
```

FIG.1A

```
 |                                                                                              
 F   L   K   S   P   A   Y   R   D   L   A   A   Q   A   S   A   T   S   T   S       189
TTC CTC AAG TCA CCA GCT TAT CGC GAC CTG GCT GCC CAA GCC TCG GCC ACT TCC ACC TCT       567

A   P   S   G   S   P   A   E   P   S   H   T   *                                    202
GCA CCC AGC GGC AGC GGC CCA GCT GAG CCT TCA CAC ACT TGA                               606

GCCTCCGCAGCAACCTAGAGAGCCATCGGGAAGAGAGGTGGAGTGCCCGTCCCTAAAGCAGCTGCCCTGTGTCGGAGGC

AGATCCTGTGCAGCAAGTGCAAGAGGATAGTGGAAGGACAGACGGACATCCCATCCCGCAGCTTGAGTGCGAAGAACCC

CCTCTCCTCCAGATACTGTGGTGGGCCAGTGTAGGAGAGACTCCTCATTTCCAGGACCTGTGACTGAGGGCTGACGACA

AGGCTGGCGCGGGTGCTCTGGGGGGAACGGGTGGCCCAGAACTTATACTTTTTACCAGGGCACACACAAAGGGATGCTGG

GTGGTTGGGAACCATGAGAACAGGAGCCAGAACAGTCAGTTATTTAAGGGCCAGACAGTCGGCTTTGGTCCCCGTCTTGAT

TTCCTCACTCCTGGACTGGGCCTAGAAAAGGCTGTGTGTGTGGAACCTTCATTTCCTGCCCTTGCCTTCCCAGGGACA

CCCAGGGCCCCCGAGCTGAGGCTTCTTAATATTCCTGTGCTCATTTCTTGCCGTCTCACAGAGGTCAATGAGTCTGTCTG

ATTCTTGGCCCAGATGAGATTTCTATACCTCAAAAAACCGGCCTGTGAGCCCCTTTCCGGGTCAATGATGAATCCTGCA

AAAGAAGCCATTCTGCTCATGGGACCCTAAGCTGGGTGCTCTCCATGCCGTCTTGTAGGTGCCCCCTGCCTTCACCT

TTGCAGCAGGGTCTGCTTGTGAACAGGGCTAACTGAGAAGTCTTACTGGGCCCTGCGCTCCTTGGAAGATGGGGTCTAA

GGAGGGAGGTGGGAGGAAGGAGACTTCCGGCACAGGGCCAGCACTCATGTCCAGCAGGTGAGCTAAGGGAGAGAAGTC
```

FIG.1B

ATTGAAAAATCCATCTAGGAGCCCAAAAGACTAGCTGAAGTCAAACCAGTTCTCTTTGTGGGTATGAAAATGGGGAAAA

GTGTCTCCTACCCCTCACCCTGGTGGAAGGGAGCCTTGTGCTTCTTCCTGTTGACATGAGATGCCCACTGTAGTTAG

GGGAGAAGCCCGTCAAGGACCAAGAAAGCTCTGGAACAGAAGTTAGCTCAGCCAAGGAGTATTGCAGATGTGCGGGGA

GGGCTGCCTGGAAGGATGGGGCCGGGGGGAAACCAACTTGCCTGCCTATCACTTCTGAGTCTTACCGAACAAACTTCCA

AGTTGGGACTTCCAGCACCAGCCACCGAGACGGAGACCTAGGTTGTTCCCCTGCACTTGAGGTTTCTCCGGAGAGA

ACTCTTTAAGTATAATATTGTGTTCTGTGTTGTGTGCCGATTGTCTCGCTGCTATTGTTATTTATTGTGGTTTGTTT

GCCTGTACTGAAGAGCCTCAGCTGCCTGAGCTGCTGCCTGATCACGCCTCCTCCCTACCAGACTCTACCTCTGCAAGCCTTG

GGAATCACTGAGGGCTGGGGGGGGGAACGGGACACGGGACTCCCCACTGTTAATATTTATTTATTGTTAACAA

AGGGAGCTGGGTTCCTTTATCAGCAGTGTATGTGATCACTGTTTTCTGTTTGAGCATGTTATATTCTTGTAAAAAAAC

CTGAAAATAAAACTCAAAAATAAAAAAAAAAAAGGGCGGCCGC

FIG.1C

```
                                                                                    10
CCATCCTGCCTACTACGTGCTGCCTGCCCTGGCCCCGAGCC ATG TGC CGC ACC CTG GCC GCC TTC CCC ACC    68
                                          M   C   R   T   L   A   A   F   P   T

T   C   L   E   R   A   K   E   F   K   T   R   L   G   I   F   L   H   K   S      30
ACC TGC CTG GAG AGA GCC AAA GAG TTC AAG ACA CGT CTG GGG ATC TTT CTT CAC AAA TCA     128

E   L   G   C   D   T   G   S   T   G   K   F   E   W   G   S   K   H   S   K      50
GAG CTG GGC TGC GAT ACT GGG AGT ACT GGC AAG TTC GAG TGG GGC AGT AAA CAC AGC AAA     188

E   N   R   F   S   E   D   V   L   G   W   R   E   S   F   D   L   L   L   L      70
GAG AAT AGA TTC TCA GAA GAT GTG CTG GGG TGG AGA GAG TCG TTC GAC CTG CTG CTG CTG     248
                                                                 *   *   *   *

S   K   N   G   V   A   F   H   A   C   E   E   F   K   T   S   E   E   E          90
AGC AGT AAA AAT GGA GTG GCT GCC TTC CAC GCT TGT GAG GAG TTC AAG ACA AGT GAG GAG     308
         *           *   *       *       *   *   *       *   *

N   L   E   F   W   L   W   L   K   K   I   R   S   A   T   K   L              110
AAC CTG GAG TTC TGG CTG TGG CTG AAG AAG ATC CGA TCA GCT ACC AAG CTG               368

A   S   R   A   H   Q   I   F   E   E   F   I   C   S   E   A   P   K   E   V     130
GCC TCC AGG GCA CAC CAG ATC TTT GAG GAG TTC ATT TGC AGT GAG GCC CCT AAA GAG GTC     428

N   I   D   H   E   T   R   E   L   T   R   M   N   L   Q   T   A   T              150
AAC ATT GAC CAT GAG ACC CGC GAG CTG ACG AGG ATG AAC CTG CAG ACT GCC ACA               488
```

FIG. 2A

```
                                                *  *
         *   *           *  *              *    |  |
 |       |   |           |  |              |    |  |
 C   F   D   A   A   Q   G   K   T   R   T   L   M   E   K   D   S   Y   P   R      170
TGC TTT GAT GCG GCT CAG GGG AAG ACA CGT ACC CTG ATG GAG AAG GAC TCC TAC CCA CGC      548
                     *
 |                   |
 F   L   K   S   P   A   Y   R   D   L   A   A   Q   A   S   A   A   S   A   T      190
TTC CTG AAG TCG CCT GCT TAC CGG GAC CTG GCT GCC CAA GCC TCA GCC GCC TCT GCC ACT      608

L   S   S   C   S   L   D   E   P   S   H   T   *                                  203
CTG TCC AGC TGC AGC CTG GAC GAG CCC TCA CAC ACC TGA                                  647

GTCTCCACGGGCAGTGAGGAAGCCAGCCCGGGAAGAGAGGTTGAGTCACCCATCCCCCAGTGGCTGCCCCTGTGTGGGAG    726

GCAGGTTCTAAGCCCGAATTC                                                               746
```

FIG.2B

RATH GENES AND POLYPEPTIDES AND METHODS FOR THE TREATMENT AND DIAGNOSIS OF IMMUNE DISORDERS

This is a division, of application Ser. No. 08/870,815, filed Jun. 6, 1997, now U.S. Pat. No. 6,020,142, which is a continuation-in-part of application Ser. No. 08/726,228, filed Oct. 4, 1996, now U.S. Pat. No. 5,846,780.

1. INTRODUCTION

The present invention relates, first, to the identification of novel nucleic acid molecules and polypeptides encoded by such nucleic acid molecules, or degenerate variants thereof, that participate in the modulation of T cell activity, including, but not limited to T helper (TH) cell and TH cell subpopulation activity. Such nucleic acids and polypeptides are important, for example, in developing diagnostics and targets for intervention therapy. Specifically, the nucleic acid molecules of the present invention include the genes corresponding to a novel mammalian gene family termed herein the RATH gene family, which includes, but is not limited to, novel genes referred to herein as the RATH1.1 genes. Sequence analysis indicates that RATH genes are novel genes belonging to the RGS ("regulator of G-protein signalling") gene family, a gene family which encodes gene products involved in G-protein-mediated signal transduction that act to inhibit G-protein-mediated signalling at the level of receptor/G-protein interaction or the G protein α subunit itself. It is demonstrated herein that the RATH1.1 gene product acts as a mediator of signal transduction events. It is further demonstrated that the RATH1.1 gene product acts to participate in the regulation of integrin-mediated cell adhesion and, further, strongly interacts with calpactin, a molecule known to affect cellular signalling and a number of other cellular processes. The discovery of the RATH1.1 gene represents the first identification of a T cell specific—and more particularly, a T helper (TH) cell subpopulation specific—RGS gene and gene product. The present invention further relates to methods for the diagnostic evaluation, prognosis and treatment of immune disorders involving T cell activation, including, but not limited to, TH cell and TH cell subpopulation activation. Such immune disorders include, but are not limited to chronic inflammatory diseases and disorders, such as Crohn's disease, reactive arthritis, including Lyme disease, insulin-dependent diabetes, organ-specific autoimmunity, including multiple sclerosis, rheumatoid arthritis, inflammatory bowel disease, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy. The present invention still further relates to methods of treating the above diseases by administering compounds which modulate RATH proteins and/or RATH gene activity. The present invention still further relates to methods for the identification of compounds which modulate (antagonize or agonize) RATH gene product.

2. BACKGROUND OF THE INVENTION

Two distinct types of T lymphocytes are recognized: $CD8^+$ cytotoxic T lymphocytes (CTLs) and $CD4^+$ helper T lymphocytes (TH cells). CTLs recognize and kill cells which display foreign antigens of their surfaces. CTL precursors display T cell receptors that recognize processed peptides derived from foreign proteins, in conjunction with class I MHC molecules, on other cell surfaces. This recognition process triggers the activation, maturation and proliferation of the precursor CTLs, resulting in CTL clones capable of destroying the cells exhibiting the antigens recognized as foreign.

Human and murine TH cells are involved in both humoral and cell-mediated forms of effector immune responses. With respect to the humoral, or antibody, immune response, antibodies are produced by B lymphocytes through interactions with TH cells. In murine cells, extracellular antigens are endocytosed by antigen-presenting cells (APCs), processed, and presented preferentially in association with class II major histocompatibility complex (MHC) molecules to $CD4^+$ class II MHC-restricted TH cells. These TH cells in turn activate B lymphocytes, resulting in antibody production.

The cell-mediated, or cellular, immune response, functions to neutralize microbes which inhabit intracellular locations. Foreign antigens, such as, for example, viral antigens, are synthesized within infected cells and presented on the surfaces of such cells in association with class I MHC molecules. This, then, leads to the stimulation of the $CD8^+$ class I MHC-restricted CTLs.

Some agents, such as mycobacteria, which cause tuberculosis and leprosy, are engulfed by macrophages and processed in vacuoles containing proteolytic enzymes and other toxic substances. While these macrophage components are capable of killing and digesting most microbes, agents such as mycobacteria survive and multiply. The agents' antigens are processed, though, by the macrophages and presented preferentially in association with class II MHC molecules to $CD4^+$ class II MHC-restricted TH cells, which become stimulated to secrete interferon-γ, which, in turn, activates macrophages. As a result of such activation, the cells exhibit increased bacteriocidal ability.

Murine TH cells are composed of at least two distinct subpopulations, termed TH1 and TH2 cell subpopulations. Evidence suggests that TH1 and TH2 subtypes represent extremely polarized populations of TH cells. While such subpopulations were originally discovered in murine systems (reviewed in Mosmann, T. R. and Coffman, R. L., 1989, Ann. Rev. Immunol. 7:145), the existence of TH1- and TH2-like subpopulations has also been established in humans (Del Prete, A. F. et al., 1991, J. Clin. Invest. 88:346; Wiernenga, E. A. et al., 1990, J. Imm. 144:4651; Yamamura, M. et al., 1991, Science 254:277; Robinson, D. et al., 1993, J. Allergy Clin. Imm. 92:313). While TH1-like and TH2-like cells can represent the most extremely polarized TH cell subpopulations, other TH cell subpopulations, such as TH0 cells (Firestein, G. S. et al., 1989, J. Imm. 143:518), which represent TH cells which have characteristics of TH1 and TH2 cell subpopulations.

TH1-like and TH2-like cells appear to function as part of the different effector functions of the immune system (Mosmann, T. R. and Coffmann, R. L., 1989, Ann. Rev. Imm. 7:145). Specifically, TH1-like cells direct the development of cell-mediated immunity, triggering phagocyte-mediated host defenses, and are associated with delayed hypersensitivity. Accordingly, infections with intracellular microbes tend to induce TH1-type responses. TH2 cells drive humoral immune responses, which are associated with, for example, defenses against certain helminthic parasites, and are involved in antibody and allergic responses.

It has been noted that the ability of the different TH cell types to drive different immune effector responses is due to the exclusive combinations of cytokines which are expressed within a particular TH cell subpopulation. For example, TH1 cells are known to secrete interleukin-2 (IL-2), interferon-γ (IFN-γ), and lymphotoxin, while TH2 cells secrete interleukin-4 (IL-4), interleukin-5 (IL-5), and interleukin-10 (IL-10).

It has recently been noted that, in addition to $CD4^+$ TH cells, $CD8^+$ CTLs can, under certain conditions, also exhibit TH1-like or TH2-like cytokine profiles (Seder, R. A. et al., 1995, J. Exp. Med. 181:5–7; Manetti, R. et al., 1994, J. Exp. Med. 180:2407–2411; Maggi, E. et al., 1994, J. Exp. Med. 180:489–495). While the precise functional role of such $CD8^+$ TH-like cells is currently unknown, these cell subpopulations appear to have great relevance to immune responses against infectious agents such as viruses and intracellular parasites.

Failure to control or resolve an infectious process often results from an inappropriate immune response. Such an inappropriate immunological response can include, for example, atopic conditions (i.e., IgE-mediated allergic conditions) such as asthma, allergy, including allergic rhinitis, dermatitis, including psoriasis, pathogen susceptibilities, chronic inflammatory disease, organ-specific autoimmunity, graft rejection and graft versus host disease. Failure to resolve infestation by helminthic parasites is an example of a condition which may result in an inappropriate immune response.

Further, while TH1-mediated inflammatory responses to many pathogenic microorganisms are beneficial, such responses to self antigens are usually deleterious. It has been suggested that the preferential activation of TH1-like responses is central to the pathogenesis of such human inflammatory autoimmune diseases as multiple sclerosis and insulin-dependent diabetes. For example, TH1-type cytokines predominate in the cerebrospinal fluid of patients with multiple sclerosis, pancreases of insulin-dependent diabetes patients, thyroid glands of Hashimoto's thyroiditis, and gut of Crohn's disease patients, suggesting that such patients mount a TH1-like, not a TH2-like, response to the antigen(s) involved in the etiopathogenesis of such disorders.

Accordingly, it has become increasingly important to identify T cell specific genes, gene products, in particular, TH cell and TH cell subpopulation specific genes and gene products, for use as targets for drug intervention therapy.

3. SUMMARY OF THE INVENTION

The present invention relates, first, to the identification of novel nucleic acid molecules and proteins encoded by such nucleic acid molecules, or degenerate variants thereof, that participate in the modulation of signal transduction events, including but not limited to, G-protein-mediated signal transduction events. For example, such genes can be involved in T cell activity, including, but not limited to T helper (TH) cell and TH cell subpopulation activity. Specifically, the nucleic acid molecules of the present invention include the genes corresponding to a mammalian gene family termed herein the RATH gene family, which includes, but is not limited to, genes referred to herein as RATH1.1 genes.

In particular, the compositions of the present invention include nucleic acid molecules (e.g., RATH genes), including recombinant DNA molecules, cloned genes or degenerate variants thereof, especially naturally occurring variants, which encode novel RATH gene products, and antibodies directed against such RATH gene products or conserved variants or fragments thereof. The compositions of the present invention additionally include cloning vectors, including expression vectors, containing the nucleic acid molecules of the invention and hosts which have been transformed with such nucleic acid molecules.

The nucleic acid sequence of the murine RATH1.1 (also referred to as femtR11) gene is provided. A 2278 bp RATH1.1 cDNA was deposited on Jul. 30, 1996 with the American Type Culture Collection (ATCC), bearing ATCC Accession No. 98116. The amino acid sequence of the predicted full length RATH1.1 gene product does not contain either a recognizable transmembrane domain or a signal sequence, suggesting that the RATH1.1 gene product is an intracellular or membrane-associated gene product. The RATH1.1 gene produces a transcript of approximately 3 kb and encodes a protein of 201 amino acids with a molecular weight of approximately 22.6 kD, the sequence of which is provided. Transcripts were detected in stimulated TH cell subpopulations, in a TH1-specific fashion.

The nucleic acid sequence of the human RATH1.1 gene is also provided. Like the murine RATH1.1 gene product, human RATH1.1 contains neither a recognizable transmembrane domain nor a signal sequence and encodes an intracellular or membrane-associated gene product. The human RATH1.1 gene product encodes a protein of 202 amino acid residues, the sequence of which is provided.

Sequence analysis indicates that the RATH genes are novel genes having an RGS ("regulator of G-protein signalling") motif. The RGS motif is found at approximately amino acid residue 60 to approximately amino acid residue 179, and more specifically, approximately amino acid residue 68 to approximately amino acid residue 176 in the RATH1.1 gene product depicted in FIGS. 1A–1C, and at approximately amino acid residue 61 to 180, and more specifically, approximately amino acid residue 69 to approximately 177, and even more specifically approximately amino acid residue 69 to approximately amino acid residue 171, in the RATH1.1 gene product depicted in FIGS. 2A–2B.

RATH1.1 genes belong to a gene family, termed herein the RATH gene family, which encodes RGS-containing gene products involved in G-protein-mediated signal transduction that act to inhibit G-protein-mediated signalling at the level of receptor/G-protein interaction or the G protein α subunit itself. The RATH1.1 genes of the RATH gene family represent the first identification of T cell specific—and more particularly, T helper (TH) cell subpopulation specific—RGS genes and gene products.

The mammalian RATH genes shown herein are expressed in a highly regulated and restricted manner. Specifically, murine RATH1.1 is expressed in a highly TH1-inducible manner. That is, the RATH1.1 gene is highly upregulated in stimulated TH cell subpopulations (that is, TH1 or TH1-like cell subpopulations) and appears to be absent from, or present in very low levels within, other cell types.

The mammalian RATH gene products are demonstrated herein to act as mediators of signal transduction, including, but not limited to, G-protein-mediated signal transduction. Further, it is demonstrated herein that one of the effector functions of the the mammalian RATH gene products is to act as regulators of integrin-coupled cell adhesion. In addition, the mammalian RATH gene products are shown to strongly interact with calpactin, a molecule known to influence a number of important cellular processes.

The present invention further relates to methods for the diagnostic evaluation and prognosis of immune disorders involving T cell activation, including, but not limited to, TH cell and TH cell subpopulation activation. Such immune disorders include, but are not limited to chronic inflammatory diseases and disorders, such as Crohn's disease, reactive arthritis, including Lyme disease, insulin-dependent diabetes, organ-specific autoimmunity, including multiple sclerosis, rheumatoid arthritis, inflammatory bowel disease, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy. The present invention also relates to methods for the identification of subjects having a predisposition to such conditions. For example, nucleic acid molecules of the invention can be used as diagnostic hybridization probes or as primers for diagnostic PCR analysis for the identification of RATH gene mutations, allelic variations and regulatory defects in a RATH gene.

Further, methods and compositions are presented for the treatment of immune disorders involving T cell activation, including, but not limited to, TH cell and TH cell subpopulation activation, such as those listed above. Methods and compositions are also presented for the modulation of signal transduction-related or induced cellular events, including, but not limited to, G-protein-mediated signal transduction events. Such events include, but are not limited to, such cellular processes as cell migration, cell adhesion, cell proliferation, cell differentiation, cell activation, factor release, endocytosis, exocytosis, cytoskeletal rearrangement, membrane trafficking, and changes in cell membrane properties, such as pseudopod formation. Such methods and compositions are capable of modulating the level of RATH gene expression and/or the level of RATH gene product activity.

Still further, the present invention relates to methods for the use of RATH gene and/or RATH gene products for the identification of compounds which modulate RATH gene expression and/or the activity of RATH gene products. Such assays include, but are not limited to assays which measure RATH mRNA and/or gene product levels, and assays which measure levels of RATH gene product activities, such as, for example, the ability of RATH gene product to accelerate the rate of GTP to GDP replacement on G alpha subunits of G proteins, the effect of RATH gene product on integrin-mediated cell adhesion, and the ability of RATH gene product to bind calpactin.

Such compounds can be used as agents to control, prevent, treat and/or ameliorate (hereinafter referred to as "control") the severity of disorders, including immune disorders, and/or to modulate cellular processes, such as, for example, signal transduction-mediated cellular processes, such as those listed above.

4. DESCRIPTION OF THE FIGURES

FIGS. 1A–1C. Murine RATH1.1 nucleotide and amino acid sequence. Top line: RATH1.1 amino acid sequence (SEQ ID NO:2); bottom line: RATH1.1 nucleotide sequence (SEQ ID NO:1). An asterisk above an amino acid residue refers to an amino acid residue which is conserved in a property-wise fashion within the RGS motif domain. A vertical line above an amino acid residue refers to an amino acid residue which is conserved by identity within the RGS domain.

FIGS. 2A–2B. Human RATH1.1 nucleotide and amino acid sequence (SEQ ID NO:4). Top line: RATH1.1 amino acid sequence; bottom line: RATH1.1 nucleotide sequence (SEQ ID NO:3). An asterisk above an amino acid residue refers to an amino acid residue which is conserved in a property-wise fashion within the RGS motif domain. A vertical line above an amino acid residue refers to an amino acid residue which is conserved by identity within the RGS domain.

5. DETAILED DESCRIPTION OF THE INVENTION

Described herein are the identification of novel mammalian genes, the RATH genes, including the RATH1.1 gene, which are involved in the control of immune disorders by modulating T cell activity, including, but not limited to, TH cell and TH cell subpopulation activity. Such immune disorders include, but are not limited to chronic inflammatory diseases and disorders, such as Crohn's disease, reactive arthritis, including Lyme disease, insulin-dependent diabetes, organ-specific autoimmunity, including multiple sclerosis, rheumatoid arthritis, inflammatory bowel disease, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy. Such genes and gene products are also involved in modulation of cellular proceses, such as signal transduction-related or induced cellular processes, including, but not limited to, G-protein-mediated signal transduction events. Such events include, but are not limited to, such cellular processes as cell migration, cell adhesion, cell proliferation, cell differentiation, cell activation, factor release, endocytosis, exocytosis, cytoskeletal rearrangement, membrane trafficking, and changes in cell membrane properties, such as pseudopod formation.

Specifically described are recombinant mammalian RATH DNA molecules, cloned genes, or degenerate variants thereof. The compositions of the present invention further include RATH gene products (e.g., proteins) that are encoded by the RATH gene. Also described herein are antibodies against RATH gene products (e.g., proteins), or conserved variants or fragments thereof, and nucleic acid probes useful for the identification of RATH gene mutations and the use of such nucleic acid probes in diagnosing immune disorders involving T cell activation, including TH cell and TH cell subpopulation activation, such as those listed above.

Further described are methods for the use of the RATH gene and/or RATH gene products in the identification of compounds which modulate the activity of the RATH gene product. Methods are also described for the treatment of immune disorders involving T cell activation, including TH cell and TH cell subpopulation activation, via modulation of RATH gene expression and/or activity.

The RATH1.1 nucleic acid compositions of the invention are described in the Example presented, below, in Section 6. Functional characaterization of the RATH gene and gene product is presented in the Examples of Sections 7 through 9.

5.1. THE RATH GENE

RATH genes, shown in FIGS. 1A–1C and 2A–2B, are novel RGS genes which are regulated in a TH-restricted manner, specifically, in a TH1 or TH-1-like inducible manner. RATH1.1 is an exemplary RATH gene and represents the first example of a T cell specific RGS-containing gene, more particularly a TH cell subpopulation specific gene. As such, RATH genes can be involved in T cell activity, including TH cell and TH cell subpopulation activation.

Nucleic acid sequences of the identified RATH gene are described herein. As used herein, "RATH gene" refers to (a) a gene containing the DNA sequence shown in FIGS. 1A–1C (SEQ ID NO:1) or FIGS. 2A–2B (SEQ ID NO:3) or contained in the cDNA clone within *E. coli* femtR11A as deposited with the American Type Culture Collection (ATCC) on Jul. 30, 1996, bearing ATCC Accession No. 98116; (b) any DNA sequence that encodes the amino acid sequence shown in FIGS. 1A–1C (SEQ ID NO:2) or FIGS. 2A–2B (SEQ ID NO:4) or encoded by the cDNA clone within *E. coli* femtR11A, as deposited with the ATCC (ATCC Accession No. 98116) on Jul. 30, 1996; (c) any DNA sequence that hybridizes to the complement of the DNA sequences that encode the amino acid sequences shown in FIGS. 1A–1C (SEQ ID NO:2) or FIGS. 2A–2B (SEQ ID NO:4), or contained in the cDNA clone within *E. coli* femtR11A as deposited with the ATCC (ATCC Accession No. 98116), under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) or (d) any DNA sequence that hybridizes to the complement of the DNA sequences that encode the amino acid sequence shown in FIGS. 1A–1C (SEQ ID NO:2) or FIGS. 2A–2B (SEQ ID NO: 4), or contained in the cDNA clone within *E. coli* femtR11A as deposited with the ATCC (ATCC Accession No. 98116), under less stringent conditions, such as moderately stringent conditions, e.g., washing in 0.2×SSC/0.1% SDS at 42° C. (Ausubel et al., 1989, supra), and encodes a gene product functionally equivalent to a RATH gene product encoded by sequences contained in the cDNA clone within *E. coli* femtR11A, or sequences shown in FIGS. 1A–1C (SEQ ID NO:2) or FIGS. 2A–2B (SEQ ID NO: 4).

As used herein, the term "RATH gene" may also refer to fragments and/or degenerate variants of DNA sequences (a) through (d), especially naturally occurring variants thereof. Such fragments include, for example, nucleotide sequences that encode portions of the RATH gene products of the invention that correspond to RATH gene product functional domains. One embodiment of such a RATH gene fragment comprises a nucleic acid molecule which encodes the RGS domain contained within the amino acid sequence shown in FIGS. 1A–1C or within the amino acid sequence shown in FIGS. 2A–2B (SEQ ID NO:4). Additional RATH gene product functional domains can include, but are not limited to, RATH gene product domains that bind to RATH gene product interactors such as, for example, calpactin.

RATH gene fragments can also include, for example, nucleotide sequences that encode portions of the RATH gene products of the invention wherein such gene products lack one or more of the RATH gene product functional domains. One embodiment of such a RATH gene fragment comprises a nucleic acid molecule which encodes the amino acid sequence depicted in FIGS. 1A–1C (SEQ ID NO:2) or FIGS. 2A–2B (SEQ ID NO:4), wherein the amino acid sequence lacks the RGS domain depicted therein. Another embodiment of such a RATH gene fragment comprises a nucleic acid molecule which encodes the amino acid sequence depicted in FIGS. 1A–1C (SEQ ID NO:2) or FIGS. 2A–2B, (SEQ ID NO: 4) wherein the amino acid sequence lacks the calpactin-binding domain depicted therein.

A RATH gene sequence preferably exhibits at least about 80% overall similarity at the nucleotide level to the nucleic acid sequence depicted in FIGS. 1A–1C, (SEQ ID NO:1) more preferably exhibits at least about 85–90% overall similarity to the FIGS. 1A–1C nucleic acid sequence and most preferably exhibits at least about 95% overall similarity to the FIGS. 1A–1C nucleic acid sequence (SEQ ID NO:1).

In one embodiment, the RATH genes of the invention are expressed in a TH specific or enhanced manner, and more preferably, in a TH cell subpopulation (e.g., TH1 or TH1-like cell subpopulation) specific, restricted or enhanced manner.

The RATH gene sequences of the invention further include isolated nucleic acid molecules which hybridize under highly stringent or moderate stringent conditions to at least about 6, preferably at least about 12, more preferably at least about 18, consecutive nucleotides of the RATH gene sequences of (a)–(d).

The invention also includes nucleic acid molecules, preferably DNA molecules, that hybridize to, and are therefore the complements of, the DNA sequences (a) through (d), in the preceding paragraph. Such hybridization conditions may be highly stringent or moderately stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as RATH gene antisense molecules useful, for example, in RATH gene regulation (for example, as antisense primers in amplification reactions of RATH gene nucleic acid sequences. With respect to RATH gene regulation, such techniques can be used to modulate signal transduction-mediated events, including, for example, G-protein-mediated signal transduction events such as T cell activation or inhibition.

Further, such sequences may be used as part of ribozyme and/or triple helix sequences, also useful for RATH gene regulation. Still further, such molecules may be used as components of diagnostic methods whereby, for example, the presence of a particular RATH allele or alternatively spliced RATH transcript responsible for causing or predisposing one to an immune disorder involving T cell activation may be detected.

Still further, the invention encompasses RATH gene sequences as part of screens in an engineered yeast system, including, but not limited to, the yeast two hybrid systems described herein.

The invention also encompasses (a) DNA vectors that contain any of the foregoing RATH sequences and/or their complements (e.g., antisense); (b) DNA expression vectors that contain any of the foregoing RATH coding sequences operatively associated with a regulatory element that directs the expression of the coding sequences; and (c) genetically engineered host cells that contain any of the foregoing RATH coding sequences operatively associated with a regulatory element that directs the expression of the coding sequences in the host cell. As used herein, regulatory elements include, but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

The invention includes fragments of any of the DNA sequences disclosed herein. The invention further includes nucleic acid sequences encoding the RATH gene products and RATH gene product fusions described, below, in Section 5.2. The invention still further includes nucleic acid analogs, including but not limited to peptide nucleic acid analogues, equivalent to the nucleic acid molecules described herein. "Equivalent" as used in this context refers to nucleic acid analogs that have the same primary base sequence as the nucleic acid molecules described above. Nucleic acid analogs and methods for the synthesis nucleic acid analogs are well known to those of skill in the art. See, e.g., Egholm, M. et al., 1993, Nature 365:566–568; and Perry-O'Keefe, H. et al., 1996, Proc. Natl. Acad. USA 93:14670–14675, both of which are incorporated herein by reference in their entirety.

In addition to the RATH gene sequences described above, homologs of such sequences, exhibiting extensive homology to one or more of domains of the RATH gene product present in other species can be identified and readily isolated, without undue experimentation, by molecular biological techniques well known in the art. Further, there can exist homolog genes at other genetic loci within the genome that encode proteins which have extensive homology to one or more domains of the RATH gene product. These genes can also be identified via similar techniques. Still further, there can exist alternatively spliced variants of the RATH1.1 gene.

As an example, in order to clone a human RATH gene homolog or variants using isolated murine RATH gene sequences as disclosed herein, such murine RATH gene sequences are labeled and used to screen a cDNA library constructed from mRNA obtained from appropriate cells or tissues (e.g., peripheral lymphocytes, activated T cells, preferably activated TH cells) derived from the organism (in this case, human) of interest. With respect to the cloning of such a human RATH homolog, a human activated T cell cDNA library may, for example, be used for screening. In particular, such a cDNA library can be one made from human peripheral lymphocytes which are stimulated with phytohemagglutinin (PHA) for 48 hours.

The hybridization and wash conditions used should be of a low stringency when the cDNA library is derived from a different type of organism than the one from which the labeled sequence was derived. Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

With respect to the cloning of a human RATH homolog, using murine RATH1.1 sequences, for example, various stringency conditions which promote DNA hybridization can be used. For example, hybridization in 6× SSC at about 45° C., followed by washing in 2×SSC at 50° C. may be used. Alternatively, the salt concentration in the wash step can range from low stringency of about 5×SSC at 50° C., to moderate stringency of about 2×SSC at 50° C., to high stringency of about 0.2×SSC at 50° C. In addition, the temperature of the wash step can be increased from low stringency conditions at room temperature, to moderately stringent conditions at about 42° C., to high stringency conditions at about 65° C. Other conditions include, but are not limited to, hybridizing at 68° C. in 0.5 M $NaHPO_4$ (pH7.2)/1 mM EDTA/7% SDS, or hybridization in 50% formamide/0.25M $NaHPO_4$ (pH 7.2)/0.25 M NaCl/1 mM EDTA/7% SDS; followed by washing in 40 mM $NaHPO_4$ (pH 7.2)/1 mM EDTA/5% SDS at 50° C. or in 40 mM $NaHPO_4$ (pH7.2) 1 mM EDTA/1% SDS at 50° C. Both temperature and salt may be varied, or alternatively, one or the other variable may remain constant while the other is changed.

Alternatively, the labeled fragment may be used to screen a genomic library derived from the organism of interest, again, using appropriately stringent conditions well known to those of skill in the art.

Further, a RATH gene homolog may be isolated from nucleic acid of the organism of interest by performing PCR using two degenerate oligonucleotide primer pools designed on the basis of amino acid sequences within the RATH gene product disclosed herein. The template for the reaction may be cDNA obtained by reverse transcription of mRNA prepared from, for example, human or non-human cell lines or tissue known or suspected to express a RATH gene allele.

The PCR product may be subcloned and sequenced to ensure that the amplified sequences represent the sequences of a RATH gene nucleic acid sequence. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may be utilized to isolate full length cDNA sequences. For example, RNA may be isolated, following standard procedures, from an appropriate cellular or tissue source (e.g., one known, or suspected, to express the RATH gene, such as, for example, lymphocytes and activated T cells, especially activated TH cells). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

RATH gene sequences may additionally be used to isolate mutant RATH gene alleles. Such mutant alleles may be isolated from individuals either known or proposed to have a genotype which contributes to the symptoms of immune disorders involving T cell activity, including TH cell and TH cell subpopulation activity, such as those listed above. Mutant alleles and mutant allele products may then be utilized in the screening, therapeutic and diagnostic systems described herein. Additionally, such RATH gene sequences can be used to detect RATH gene regulatory (e.g., promoter) defects which can affect such immune disorders.

A cDNA of a mutant RATH gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant RATH allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant RATH allele to that of the normal RATH allele, the mutation(s) responsible for the loss or alteration of function of the mutant RATH gene product can be ascertained.

Alternatively, a genomic library can be constructed using DNA obtained from an individual suspected of or known to carry the mutant RATH allele, or a cDNA library can be constructed using RNA from a tissue known, or suspected, to express the mutant RATH allele. The normal RATH gene or any suitable fragment thereof may then be labeled and used as a probe to identify the corresponding mutant RATH allele in such libraries. Clones containing the mutant RATH gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant RATH allele in an individual suspected of or known to carry such a mutant allele. In this manner, gene products made by the putatively mutant tissue may be expressed and screened using standard antibody screening techniques in conjunction with antibodies raised against the normal RATH gene product, as described, below, in Section 5.3. (For screening techniques, see, for example, Harlow, E. and Lane, eds., 1988, "Anti-bodies: A Laboratory Manual", Cold Spring Harbor Press, Cold Spring Harbor.) In cases where a RATH mutation results in an expressed gene product with altered function (e.g., as a result of a missense or a frameshift mutation), a polyclonal set of anti-RATH gene product antibodies are likely to cross-react with the mutant RATH gene product. Library clones detected via their reaction with such labeled antibodies can be purified and subjected to sequence analysis according to methods well known to those of skill in the art.

5.2. PROTEIN PRODUCTS OF THE RATH GENE

The present invention relates to RATH gene products, including, but not limited to RATH1.1 gene products, or peptide fragments thereof. Such gene products or peptide fragments thereof, can be prepared for a variety of uses. For example, such gene products, or peptide fragments thereof, can be used for the generation of antibodies, in diagnostic assays, for the identification of other cellular gene products involved in the modulation of T cell activity, such as, for example, T cell activation, including TH cell and TH cell subpopulation activity, such as, for example, TH cell and TH cell subpopulation activation, or for the identification of compounds which modulate the expression and/or activity of the RATH genes and gene products.

The amino acid sequence depicted in FIGS. 1A–1B (SEQ ID NO:2) represents a RATH gene product, specifically, a murine RATH1.1 gene product. The amino acid sequence depicted in FIGS. 2A–2B (SEQ ID NO:4) represents a RATH gene product, specifically, a human RATH1.1 gene product. RATH gene products, sometimes referred to herein as "RATH proteins", may additionally include those gene products encoded by the RATH gene sequences described in Section 5.1, above.

In addition, RATH gene products may include proteins that represent functionally equivalent gene products. Such an equivalent RATH gene product may contain deletions, additions or substitutions of amino acid residues within the amino acid sequence encoded by the RATH gene sequences described, above, in Section 5.1, but which result in a silent change, thus producing a functionally equivalent RATH gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

In a particular embodiment, a RATH gene product comprises the RGS motif domain contained within the amino acid sequence shown in FIGS. 1A–1C (SEQ ID NO:2). The RGS motif is found at approximately amino acid residue 60 to approximately amino acid residue 179, and more specifically, approximately amino acid residue 68 to approximately amino acid residue 176 in the RATH1.1 gene product depicted in FIGS. 1A–1C (SEQ ID NO:2).

In another particular embodiment, a RATH gene product comprises the RGS domain contained within the amino acid sequence shown in FIGS. 2A–2B (SEQ ID NO:4). The RGS motif is found at approximately amino acid residue 61 to 180, and more specifically, approximately amino acid residue 69 to approximately 177, and even more specifically approximately amino acid residue 69 to approximately amino acid residue 171, in the RATH1.1 gene product depicted in FIGS. 2A–2B (SEQ ID NO:4).

A number of amino acid changes can be made within the RATH RGS domains. Guidelines regarding conserved amino acid residues within the RGS domains are as follows. In general, a vertical line above an amino acid residue depicted in FIGS. 1A–1C (SEQ ID NO:2) or FIGS. 2A–2B (SEQ ID NO:4) refers to a residue whose identity is conserved at the corresponding position within the RGS domain of FIGS. 1A–1C (SEQ ID NO:2) or FIG. 2A–2B (SEQ ID NO:4). Further, an asterisk above an amino acid residue depicted in FIGS. 1A–1C (SEQ ID NO:2) or FIGS. 2A–2B (SEQ ID NO:4) refers to a residue which should be conserved in a property-wise fashion at the corresponding position within the RGS domain of FIGS. 1A–1C (SEQ ID NO:2) or FIGS. 2A–2B (SEQ ID NO:4).

"Functionally equivalent", as utilized herein, refers to a protein capable of exhibiting a substantially similar in vivo or in vitro activity as the endogenous RATH gene products encoded by the RATH gene sequences described in Section 5.1, above. The activity of the RATH gene product, as used herein, refers to the ability of the RATH gene product, when present in an appropriate cell type, to desensitize the cell to physiological stimuli. For example, RATH gene product, in an appropriate T cell type, will desnsitize the cell to T cell-relevant physiological stimuli, such as may, for example, occur in allergic inflammation disease or autoimmune disease. Such activity also refers to the ability of the RATH gene product, when present in an appropriate cell type, to contribute to the regulation (negative or positive) of integrin-mediated cell adhesion. Such activity also refers to the ability of the RATH gene product to bind to and interact with the calpactin molecule.

In addition, "functionally equivalent", refers to a protein capable of exhibiting substantially similar in vivo activity in yeast as the SST2 gene product which is the yeast homolog of RATH. Mutations in SST2 cause increased sensitivity and defective desensitization to the yeast α factor mating pheromone. α-factor binds to a G-protein coupled receptor and causes cells to arrest in the G1 phase of the cell cycle. A zone of inhibition assay measures pheromone sensitivity and desensitization (Dohlman et al., 1995, Mol. Cell Biol., 15:3635–3643). In this assay filter disks impregnated with alpha factor were placed on top of a lawn of cells of a MATa yeast strain to be tested. The alpha factor diffuses away form the disk into the agar creating a gradient of alpha factor concentration. Relative to wild-type cells, SST2 mutants have larger zones of growth inhibition and the cells within these halos do not desensitize to the pheromone signal by resuming growth. A "functionally equivalent" RATH would refer to a protein able to compliment the yeast SST2 mutation, including, but not limited to the ability to interact with substantially similar polypeptides in a yeast two hybrid system described herein.

Alternatively, where alteration of function is desired, deletion or non-conservative alterations can be engineered to produce altered RATH gene products. Such alterations can, for example, alter one or more of the biological functions, as described above, of the RATH gene products. Further, such alterations can be selected so as to generate RATH gene products that are better suited for expression, scale up and the like in the host cells chosen for expression. For example, cysteine residues canbe deleted or substituted with another amino acid residue in order to eliminate disulfide bridges.

A RATH gene product sequence preferably exhibits at least about 80% overall similarity at the amino acid level to the amino acid sequence depicted in FIGS. 1A–1C, more preferably exhibits at least about 90% overall similarity to the FIGS. 1A–1C amino acid sequence (SEQ ID NO:2) and most preferably exhibits at least about 95% overall similarity to the FIGS. 1A–1C amino acid sequence.

RATH gene products can also include fusion proteins comprising a RATH gene product sequence as described in this section operatively associated to a heterologous, e.g., peptide, component. Heterologous components can include, but are not limited to, sequences which faciliate isolation and purification of fusion protein, or label components. Such isolation and label components are well known to those of skill in the art.

The RATH gene products or peptide fragments thereof, may be produced by recombinant DNA technology using techniques well known in the art. Thus, methods for preparing the RATH gene polypeptides and peptides of the invention by expressing nucleic acid containing RATH gene sequences are described herein. Methods which are well known to those skilled in the art can be used to construct expression vectors containing RATH gene product coding sequences and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. Alternatively, RNA capable of encoding RATH gene product sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the RATH gene coding sequences of the invention. Such host-expression systems represent vehicles by which the coding sequences of interest may be produced and subsequently purified, but also represent cells which may, when transformed or transfected with the appropriate nucleotide coding sequences, exhibit the RATH gene product of the invention in situ. These include but are not limited to microorganisms such as bacteria (e.g., *E. coli, B. subtilis*) transformed with recombinant bacteriophage DNA, plasmid DNA or cosmid DNA expression vectors containing RATH gene product coding sequences; yeast (e.g., Saccharomyces, Pichia) transformed with recombinant yeast expression vectors containing the RATH gene product coding sequences; insect cell systems infected with recombinant virus expression vectors (e.g., baculovirus) containing the RATH gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing RATH gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the RATH gene product being expressed. For example, when a large quantity of such a protein is to be produced, for the generation of pharmaceutical compositions of RATH protein or for raising antibodies to RATH protein, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the RATH gene product coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhedrosis virus (ACNPV) is used as a vector to express foreign genes. The virus grows in *Spodoptera frugiperda* cells. The RATH gene coding sequence may be cloned individually into non-essential regions (for example the polyhedrin gene) of the virus and placed under control of an AcNPV promoter (for example the polyhedrin promoter). Successful insertion of RATH gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the RATH gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing RATH gene product in infected hosts. (E.g., See Logan & Shenk, 1984, Proc. Natl. Acad. Sci. USA 81:3655–3659). Specific initiation signals may also be required for efficient translation of inserted RATH gene product coding sequences. These signals include the ATG initiation codon and adjacent sequences. In cases where an entire RATH gene, including its own initiation codon and adjacent sequences, is inserted into the appropriate expression vector, no additional translational control signals may be needed. However, in cases where only a portion of the RATH gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, and in particular, T cell lines such as, for example, Jurkat, CTLL, HT2, Dorris, D1.1, AE7, D10.G4 and CDC25.

For long-term, high-yield production of recombinant proteins, stable expression is preferred. For example, cell lines which stably express the RATH gene product may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the RATH gene product. Such engineered cell lines may be particularly useful in screening and evaluation of compounds that affect the endogenous activity of the RATH gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni$^{2+}$ nitriloacetic acid-agarose columns and histidine-tagged proteins are selectively eluted with imidazole-containing buffers.

In instances where the mammalian cell is a human cell, among the expression systems by which the RATH gene sequences of the invention can be expressed are human artificial chromosome (HAC) systems. Such techniques are well known to those of skill in the art. See, e.g., Harrington et al., 1997, Nature Genetics 15:345–355, which is incorporated herein by reference in its entirety. RATH gene expression in HACs can utilize endogenous or heterologous RATH transcriptional and/or translational sequences.

The RATH gene products can also be expressed in transgenic animals. Animals of any species, including, but not limited to, mice, rats, rabbits, guinea pigs, pigs, micro-pigs, sheep, goats, and non-human primates, e.g., baboons, monkeys, and chimpanzees may be used to generate RATH transgenic animals. The term "transgenic" as used herein, refers to animals expressing RATH gene sequences from a different species (e.g., mice expressing human RATH gene sequences), as well as animals that have been genetically engineered to overexpress endogenous (i.e., same species) RATH gene sequences or animals that have been genetically engineered to no longer express endogenous RATH gene sequences (i.e., "knock-out" animals), and their progeny.

Any technique known in the art may be used to introduce the RATH gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

Any technique known in the art may be used to produce transgenic animal clones containing a RATH transgene, for example, nuclear transfer into enucleated oocytes of nuclei from cultured embryonic, fetal or adult cells induced to quiescence (Campbell et al., 1996, Nature 380:64–66; Wilmut et al., 1997, Nature 385:810–813).

The present invention provides for transgenic animals that carry the RATH transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the RATH gene transgene be integrated into the chromosomal site of the endogenous RATH gene, gene targeting is preferred. Briefly, when such a technique is to be utilized, vectors containing some nucleotide sequences homologous to the endogenous RATH gene are designed for the purpose of integrating, via homologous recombination with chromosomal sequences, into and disrupting the function of the nucleotide sequence of the endogenous RATH gene. The transgene may also be selectively introduced into a particular cell type, thus inactivating the endogenous RATH gene in only that cell type, by following, for example, the teaching of Gu et al. (Gu, et al., 1994, Science 265:103–106). The regulatory sequences required for such a cell-type specific inactivation will depend upon the particular cell type of interest, and will be apparent to those of skill in the art.

Methods for the production of single-copy transgenic animals with chosen sites of integration are also well known to those of skill in the art. See, for example, Bronson et al. (Bronson, S. K. et al., 1996, Proc. Natl. Acad. Sci. USA 93:9067–9072), which is incorporated herein by reference in its entirety.

Once transgenic animals have been generated, the expression of the recombinant RATH gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of RATH gene-expressing tissue, may also be evaluated immunocytochemically using antibodies specific for the RATH transgene product.

5.3. ANTIBODIES TO RATH GENE PRODUCTS

Described herein are methods for the production of antibodies capable of specifically recognizing one or more RATH gene product epitopes or epitopes of conserved variants or peptide fragments of the RATH gene products.

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a RATH gene product in an biological sample and may, therefore, be utilized as part of a diagnostic or prognostic technique whereby patients may be tested for abnormal levels of RATH gene products, and/or for the presence of abnormal forms of the such gene products. Such antibodies may also be utilized in conjunction with, for example, compound screening schemes, as described, below, in Section 5.4.2, for the evaluation of the effect of test compounds on RATH gene product levels and/or activity. Additionally, such antibodies can be used in conjunction with the gene therapy techniques described, below, in Section 5.4.3, to, for example, evaluate the normal and/or engineered RATH-expressing cells prior to their introduction into the patient.

Anti-RATH gene product antibodies may additionally be used as a method for the inhibition of abnormal RATH gene product activity. Thus, such antibodies may, therefore, be utilized as part of immune disorder treatment methods.

For the production of antibodies against a RATH gene product, various host animals may be immunized by injection with a RATH gene product, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as a RATH gene product, or an antigenic functional derivative thereof. For the production of polyclonal antibodies, host animals such as those described above, may be immunized by injection with RATH gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, both of which are incorporated herein by reference in their entirety.)

In addition, techniques have been developed for the production of humanized antibodies. (See, e.g., Queen, U.S.

Pat. No. 5,585,089, which is incorporated herein by reference in its entirety.) An immunoglobulin light or heavy chain variable region consists of a "framework" region interrupted by three hypervariable regions, referred to as complementarity determining regions (CDRs). The extent of the framework region and CDRs have been precisely defined )See, e.g., "Sequences of Proteins of Immunological Interest," Kabat, E. et al., U.S. Department of Health and Human Services, 1983). Briefly, humanized antibodies are antibody molecules from non-human species having one or more CDRs from the non-human species and a framework region from a human immunoglobulin molecule.

Alternatively, techniques described for the production of single chain antibodies (U.S. Pat. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against RATH gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

5.4. USES OF THE RATH GENE, GENE PRODUCTS, AND ANTIBODIES

Described herein are various applications of the RATH genes, the RATH gene products, including peptide fragments thereof, and of antibodies directed against the RATH gene products and peptide fragments thereof.

The RATH gene family, including, but not limited to the RATH1.1 gene which exemplifies the gene family of the present invention, is involved in the regulation of signal transduction-mediated events, such as G protein-mediated signal transduction events. For example, such genes, including, but not limited to the RATH1.1 genes, are involved the control of immune disorders involving T-cell activity. Further, among the specific RATH gene product activities are their role in T-helper cell activation, including TH cell and TH cell subpopulation activation. Such genes are also involved in the modulation of cellular processes which include, but are not limited to, cell migration, cell adhesion, cell proliferation, cell differentiation, cell activation, factor release, endocytosis, exocytosis, cytoskeletal rearrangement, membrane trafficking, and changes in cell membrane properties, such as pseudopod formation.

Such applications include, for example, prognostic and diagnostic evaluation of immune disorders involving T cell activation, including TH cell and TH cell subpopulation activation, and the identification of subjects with a predisposition to such disorders, as described, below, in Section 5.4.1.

Additionally, such applications include methods for the treatment of such immune disorders. modulation of RATH gene-mediated signal transduction events, and modulation of RATH-mediated effector functions, as described, below, in Section 25 5.4.2.

Further, such applications include assays for the identification of compounds which modulate the expression of the RATH gene and/or the activity of the RATH gene products, as described below, in Section 5.4.3. Such compounds can include, for example, compounds, including but not limited to, other cellular products or small molecule compounds, which are involved in T cell activation, especially processes relating to G-protein-mediated signal transduction in T cells; which are involved in RATH-mediated signal transduction events; or which affect effector functions of the RATH gene products such as, for example, integrin-mediated cell adhesion and/or binding to RATH interactors such as, for example, calpactin. These compounds can be used, for example, in treatment and modulation methods described herein, including, but not limited to, methods for the amelioration of immune disorders involving T cell activation, including TH cell and TH cell subpopulation activation.

5.4.1. DIAGNOSIS OF IMMUNE DISORDER ABNORMALITIES

A variety of methods can be employed for the diagnostic and prognostic evaluation of immune disorders involving T cell activation, including, but not limited to, TH cell and TH cell subpopulation activity, such as T cell activation. Such immune disorders include, but are not limited to chronic inflammatory diseases and disorders, such as Crohn's disease, reactive arthritis, including Lyme disease, insulin-dependent diabetes, organ-specific autoimmunity, including multiple sclerosis, rheumatoid arthritis, inflammatory bowel disease, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy. Methods are further provided for the identification of subjects having a predisposition to such disorders.

Such methods may, for example, utilize reagents such as the RATH gene nucleotide sequences described in Sections 5.1, and antibodies directed against RATH gene products, including peptide fragments thereof, as described, above, in Section 5.2. Specifically, such reagents may be used, for example, for: (1) the detection of the presence of RATH gene mutations, or the detection of either over- or under-expression of RATH gene mRNA relative to the non-immune disorder state or the qualitative or quantitative detection of alternatively spliced forms of RATH transcripts which may correlate with certain immune disorders or susceptibility toward such body disorders; and (2) the detection of either an over- or an under-abundance of RATH gene product relative to the non-immune disorder state or the presence of a modified (e,g., less than full length) RATH gene product which correlate s with an immune disorder state or a progression toward an immune disorder state.

The methods described herein may be performed, for example, by utilizing pre-packaged diagnostic test kits comprising at least one specific RATH gene nucleic acid or anti-RATH gene antibody reagent described herein, which may be conveniently used, e.g., in clinical settings, to screen and diagnose patients exhibiting immune disorder abnormalities and to screen and identify those individuals exhibiting a predisposition to such an immune disorder abnormality.

For the detection of RATH mutations, any nucleated cell can be used as a starting source for genomic nucleic acid. For the detection of RATH transcripts or RATH gene products, any cell type or tissue in which the RATH gene is expressed, such as, for example, activated T cells, including activated TH cells, may be utilized.

Nucleic acid-based detection techniques are described, below, in Section 5.4.1.1. Peptide detection techniques are described, below, in Section 5.4.1.2.

5.4.1.1 DETECTION OF RATH GENE NUCLEIC ACID MOLECULES

Mutations or polymorphisms within the RATH gene can be detected by utilizing a number of techniques. Nucleic acid from any nucleated cell can be used as the starting point for such assay techniques, and may be isolated according to standard nucleic acid preparation procedures which are well known to those of skill in the art.

Genomic DNA may be used in hybridization or amplification assays of biological samples to detect abnormalities involving RATH gene structure, including point mutations, insertions, deletions and chromosomal rearrangements. Such assays may include, but are not limited to, direct sequencing (Wong, C. et al., 1987, Nature 330:384–386), single stranded conformational polymorphism analyses (SSCP; Orita, M. et al., 1989, Proc. Natl. Acad. Sci. USA 86:2766–2770), heteroduplex analysis (Keen, T. J. et al., 1991, Genomics 11:199–205; Perry, D. J. & Carrell, R. W., 1992), denaturing gradient gel electrophoresis (DGGE; Myers, R. M. et al., 1985, Nucl. Acids Res. 13:3131–3145), chemical mismatch cleavage (Cotton, R. G. et al., 1988, Proc. Natl. Acad. Sci. USA 85:4397–4401) and oligonucleotide hybridization (Wallace, R. B. et al., 1981, Nucl. Acids Res. 9:879–894; Lipshutz, R. J. et al., 1995, Biotechniques 19:442–447).

Diagnostic methods for the detection of RATH gene specific nucleic acid molecules, in patient samples or other appropriate cell sources, may involve the amplification of specific gene sequences, e.g., by the polymerase chain reaction (PCR; the experimental embodiment set forth in Mullis, K. B., 1987, U.S. Pat. No. 4,683,202), followed by the analysis of the amplified molecules using techniques well known to those of skill in the art, such as, for example, those listed above. Utilizing analysis techniques such as these, the amplified sequences can be compared to those which would be expected if the nucleic acid being amplified contained only normal copies of the RATH gene in order to determine whether a RATH gene mutation exists.

Further, well-known genotyping techniques can be performed to type polymorphisms that are in close proximity to mutations in the RATH gene itself. These polymorphisms can be used to identify individuals in families likely to carry mutations. If a polymorphism exhibits linkage disequilibrium with mutations in the RATH gene, it can also be used to identify individuals in the general population likely to carry mutations. Polymorphisms that can be used in this way include restriction fragment length polymorphisms (RFLPs), which involve sequence variations in restriction enzyme target sequences, single-base polymorphisms and simple sequence repeat polymorphisms (SSLPs).

For example, Weber (U.S. Pat. No. 5,075,217, which is incorporated herein by reference in its entirety) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers which are so closely spaced exhibit a high frequency co-inheritance, and are extremely useful in the identification of genetic mutations, such as, for example, mutations within the RATH gene, and the diagnosis of diseases and disorders related to RATH mutations.

Also, Caskey et al. (U.S. Pat. No. 5,364,759, which is incorporated herein by reference in its entirety) describe a DNA profiling assay for detecting short tri and tetra nucleotide repeat sequences. The process includes extracting the DNA of interest, such as the RATH gene, amplifying the extracted DNA, and labelling the repeat sequences to form a genotypic map of the individual's DNA.

A RATH probe could additionally be used to directly identify RFLPs. Additionally, a RATH probe or primers derived from the RATH sequence could be used to isolate genomic clones such as YACs, BACs, PACs, cosmids, phage or plasmids. The DNA contained in these clones can be screened for single-base polymorphisms or simple sequence length polymorphisms (SSLPs) using standard hybridization or sequencing procedures.

Alternative diagnostic methods for the detection of RATH gene-specific mutations or polymorphisms can include hybridization techniques which involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described in Section 5.1, under conditions favorable for the specific annealing of these reagents to their complementary sequences within the RATH gene. Preferably, the lengths of these nucleic acid reagents are at least 15 to 30 nucleotides. After incubation, all non-annealed nucleic acids are removed from the nucleic acid:RATH molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled RATH nucleic acid reagents is accomplished using standard techniques well-known to those in the art. The RATH gene sequences to which the nucleic acid reagents have annealed can be compared to the annealing pattern expected from a normal RATH gene sequence in order to determine whether a RATH gene mutation is present.

Quantitative and qualitative aspects of RATH gene expression can also be assayed. For example, RNA from a cell type or tissue known, or suspected, to express the RATH gene, such as activated T cells, including activated TH cells, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the RATH gene. Such analyses may reveal both quantitative and qualitative aspects of the expression pattern of the RATH gene, including activation or inactivation of RATH gene expression and presence of alternatively spliced RATH transcripts.

In one embodiment of such a detection scheme, a cDNA molecule is synthesized from an RNA molecule of interest (e.g., by reverse transcription of the RNA molecule into cDNA). All or part of the resulting cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the RATH gene nucleic acid reagents described in Section 5.1. The preferred lengths of such nucleic acid reagents are at least 9–30 nucleotides.

For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Such RT-PCR techniques can be utilized to detect differences in RATH transcript size which may be due to normal or abnormal alternative splicing. Additionally, such techniques can be performed using standard techniques to detect quantitative differences between levels of full length and/or alternatively spliced RATH transcripts detected in normal individuals relative to those individuals exhibiting immune disorders or exhibiting a predisposition to toward such immune disorders.

In the case where detection of specific alternatively spliced species is desired, appropriate primers and/or hybridization probes can be used, such that, in the absence of such sequence, no amplification would occur. Alternatively, primer pairs may be chosen utilizing the sequence data depicted in FIGS. 1A–1C (SEQ ID NO:1) to choose primers which will yield fragments of differing size depending on whether a particular exon is present or absent from the transcript RATH transcript being utilized.

As an alternative to amplification techniques, standard Northern analyses can be performed if a sufficient quantity of the appropriate cells can be obtained. Utilizing such techniques, quantitative as well as size related differences between RATH transcripts can also be detected.

Additionally, it is possible to perform such RATH gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, NY).

5.4.1.2. DETECTION OF RATH GENE PRODUCTS

Antibodies directed against wild type or mutant RATH gene products or conserved variants or peptide fragments thereof, which are discussed, above, in Section 5.2, may also be used as immune disorder diagnostics and prognostics, as described herein. Such diagnostic methods, may be used to detect abnormalities in the level of RATH gene expression, or abnormalities in the structure and/or temporal, tissue, cellular, or subcellular location of RATH gene product. Because evidence disclosed herein indicates that the RATH gene product is an intracellular gene product, the antibodies and immunoassay methods described below have important in vitro applications in assessing the efficacy of treatments for immune disorders such as those described herein. Antibodies, or fragments of antibodies, such as those described below, may be used to screen potentially therapeutic compounds in vitro to determine their effects on RATH gene expression and RATH peptide production. The compounds which have beneficial effects on immune disorders can be identified and a therapeutically effective dose determined.

In vitro immunoassays may also be used, for example, to assess the efficacy of cell-based gene therapy for immune disorders involving T cell activation, including TH cell and TH cell subpopulation activation. Antibodies directed against RATH peptides may be used in vitro to determine the level of RATH gene expression achieved in cells genetically engineered to produce RATH peptides. Given that evidence disclosed herein indicates that the RATH gene product is an intracellular gene product, such an assessment is, preferably, done using cell lysates, membrane associated fractions or extracts. Such analysis will allow for a determination of the number of transformed cells necessary to achieve therapeutic efficacy in vivo, as well as optimization of the gene replacement protocol.

The tissue or cell type to be analyzed will generally include those which are known, or suspected, to express the RATH gene, such as, for example, activated T cells. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, New York), which is incorporated herein by reference in its entirety. The isolated cells can be derived from cell culture or from a patient. The analysis of cell taken from culture may be a necessary step in the assessment of cells to be used as part of a cell-based gene therapy technique or, alternatively, to test the effect of compounds on the expression of the RATH gene.

Preferred diagnostic methods for the detection of RATH gene products or conserved variants or peptide fragments thereof, may involve, for example, immunoassays wherein the RATH gene products or conserved variants, including gene products which are the result of alternatively spliced transcripts, or peptide fragments are detected by their interaction with an anti-RATH gene product-specific antibody.

For example, antibodies, or fragments of antibodies, such as those described, above, in Section 5.3, useful in the present invention may be used to quantitatively or qualitatively detect the presence of RATH gene products or conserved variants or peptide fragments thereof. The antibodies (or fragments thereof) useful in the present invention may, additionally, be employed histologically, as in immunofluorescence or immunoelectron microscopy, for in situ detection of RATH gene products or conserved variants or peptide fragments thereof. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the RATH gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays for RATH gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying RATH gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled RATH gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-RATH gene product antibody may be determined according to well known methods. Those skilled in the art will be able to determine operative and optimal assay conditions for each determination by employing routine experimentation.

One of the ways in which the RATH gene peptide-specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect RATH gene peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the hemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.4.2. SCREENING ASSAYS FOR COMPOUNDS THAT MODULATE RATH ACTIVITY

The following assays are designed to identify: (i) compounds that bind to RATH gene products; (ii) compounds that bind to other intracellular proteins that interact with a RATH gene product; (iii) compounds that interfere with the interaction of the RATH gene product with other intracellular proteins; and (iv) compounds that modulate the activity of RATH gene (i.e., modulate the level of RATH gene expression and/or modulate the level of RATH gene product activity). One preferred embodiment of such assays comprises assays designed to identify compounds that alter RATH binding to intracellular G-α subunits. Another preferred embodiment of such assays comprises assays which identify compounds that alter RATH binding to calpactin. Yet another preferred embodiment of such assays comprises assays which identify compounds that alter RATH-mediated integrin-coupled cell adhesion.

Assays may additionally be utilized which identify compounds which bind to RATH gene regulatory sequences (e.g., promoter sequences). See e.g., Platt, K. A., 1994, J. Biol. Chem. 269:28558–28562, which is incorporated herein by reference in its entirety, which may modulate the level of RATH gene expression. Such compounds can, for example, affect the level of RATH gene expression.

Among the compounds which can be identified herein include, but are not limited to, peptides such as, for example, soluble peptides, and small organic or inorganic molecules.

Compounds identified herein may be utilized, for example, in the control of immune disorders involving T cell activity, including, but not limited to, TH cell and TH cell subpopulation activation. Such immune disorders include, but are not limited to chronic inflammatory diseases and disorders, such as Crohn's disease, reactive arthritis, including Lyme disease, insulin-dependent diabetes, organ-specific autoimmunity, including multiple sclerosis, rheumatoid arthritis, inflammatory bowel disease, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) certain viral infections, including HIV, and bacterial infections, including tuberculosis and lepromatous leprosy, and certain neoplasms.

Compounds identified herein can also, for example, be utilized in the modulation of cellular processes which include, but are not limited to, cell migration, cell adhesion, cell proliferation, cell differentiation, cell activation, factor release, endocytosis, exocytosis, cytoskeletal rearrangement, membrane trafficking, and changes in cell membrane properties, such as pseudopod formation.

Compounds identified via assays such as those described herein may be useful, for example, in elaborating the biological function of the RATH gene product, and for ameliorating symptoms of immune disorders. Assays for testing the effectiveness of compounds, identified by, for example, techniques such as those described in Section 5.4.2.1–5.4.2.3, are discussed, below, in Section 5.4.2.4. It is to be noted that the compositions of the invention include pharmaceutical compositions comprising one or more of the compounds identified via such methods. Such pharmaceutical compositions can be formulated, for example, as discussed, below, in Section 5.6.

5.4.2.1. IN VITRO SCREENING ASSAYS FOR COMPOUNDS THAT BIND TO THE RATH GENE PRODUCT

In vitro systems may be designed to identify compounds capable of interacting with, e.g., binding to, the RATH gene products of the invention. Compounds identified may be useful, for example, in modulating the activity of wild type and/or mutant RATH gene products, may be useful in elaborating the biological function of the RATH gene product, may be utilized in screens for identifying compounds that disrupt normal RATH gene product interactions, or may in themselves disrupt such interactions.

The principle of the assays used to identify compounds that interact with the RATH gene product involves preparing a reaction mixture of the RATH gene product and the test compound under conditions and for a time sufficient to allow the two components to interact with, e.g., bind to, thus forming a complex, which can represent a transient complex, which can be removed and/or detected in the reaction mixture. These assays can be conducted in a variety of ways. For example, one method to conduct such an assay would involve anchoring RATH gene product or the test substance onto a solid phase and detecting RATH gene product/test compound complexes anchored on the solid phase at the end of the reaction. In one embodiment of such a method, the RATH gene product may be anchored onto a solid surface, and the test compound, which is not anchored, may be labeled, either directly or indirectly.

In a particular embodiment of the assays, the RATH gene product utilized comprises the RGS domain contained within the amino acid sequence depicted in FIG. 1 (SEQ ID NO:2) or FIG. 2 (SEQ ID NO:4).

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for RATH gene product or the test compound to anchor any complexes formed in solution, and a labeled antibody specific for the other component of the possible complex to detect anchored complexes.

In a particular embodiment of these assays, the test compound contains at least a portion of a G-$\alpha$ or G$\alpha$-I subunit protein such that the assay serves to identify G-$\alpha$ and/or G$\alpha$-I subunit amino acid sequences which bind to and form a complex with RATH gene product. The G-$\alpha$ and/or G-$\alpha$-I subunit sequences tested are preferably derived from G-$\alpha$ and/or G-$\alpha$-I subunits present in T cells, and are most preferably derived from T cell-specific G-$\alpha$ and/or G-$\alpha$-I subunits. G-$\alpha$ and/or G-$\alpha$-I nucleic acid and amino acid sequences are well known to those of skill in the art (see, e.g., Gilman, A., Ann. Rev. Immun., which is incorporated herein by reference in its entirety).

In another particular embodiment of these assays, the test compound contains at least a portion of a calpactin molecule such that the assay serves to identify calpactin amino acid sequences which bind to and form a complex with RATH gene product. Calpactin nucleic acid and amino acid sequences are well known to those of skill in the art (see, e.g., Waisman, D. A., 1995, Mol. Cell. Biochem., 149/150:301–322, and the references cited therein.)

5.4.2.2. ASSAYS FOR INTRACELLULAR PROTEINS THAT INTERACT WITH THE RATH GENE PRODUCT

Any method suitable for detecting protein-protein interactions may be employed for identifying RATH protein-intracellular protein interactions.

Among the traditional methods which may be employed are co-immunoprecipitation, crosslinking and co-purification through gradients or chromatographic columns. Utilizing procedures such as these allows for the isolation of intracellular proteins which interact with RATH gene products. Once isolated, such an intracellular protein can be identified and can, in turn, be used, in conjunction with standard techniques, to identify additional proteins with which it interacts. For example, at least a portion of the amino acid sequence of the intracellular protein which interacts with the RATH gene product can be ascertained using techniques well known to those of skill in the art, such as via the Edman degradation technique (see, e.g., Creighton, 1983, "Proteins: Structures and Molecular Principles", W. H. Freeman & Co., N.Y., pp.34–49). The amino acid sequence obtained may be used as a guide for the generation of oligonucleotide mixtures that can be used to screen for gene sequences encoding such intracellular proteins. Screening may be accomplished, for example, by standard hybridization or PCR techniques. Techniques for the generation of oligonucleotide mixtures and the screening are well-known. (See, e.g., Ausubel, supra, and PCR Protocols: A Guide to Methods and Applications, 1990, Innis, M. et al., eds. Academic Press, Inc., New York).

Additionally, methods may be employed which result in the simultaneous identification of genes which encode the intracellular protein interacting with the RATH protein. These methods include, for example, probing expression libraries with labeled RATH protein, using RATH protein in a manner similar to the well known technique of antibody probing of λgt11 libraries.

One method which detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to the RATH gene product and the other consists of the transcription activator protein's activation domain fused to an unknown protein that is encoded by a cDNA which has been recombined into this plasmid as part of a cDNA library. The DNA-binding domain fusion plasmid and the cDNA library are transformed into a strain of the yeast Saccharomyces cerevisiae that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, RATH gene products may be used as the bait gene product. Total genomic or cDNA sequences are fused to the DNA encoding an activation domain. This library and a plasmid encoding a hybrid of a bait RATH gene product fused to the DNA-binding domain are cotransformed into a yeast reporter strain, and the resulting transformants are screened for those that express the reporter gene. For example, and not by way of limitation, a bait RATH gene sequence, such as the open reading frame of the RATH gene, as depicted in FIG. 1 can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait RATH gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait RATH gene-GAL4 fusion plasmid into a yeast strain which contains a lacZ gene driven by a promoter which contains GAL4 activation sequence. A cDNA encoded protein, fused to GAL4 transcriptional activation domain, that interacts with bait RATH gene product will reconstitute an active GAL4 protein and thereby drive expression of the HIS3 gene. Colonies which express HIS3 can be detected by their growth on petri dishes containing semi-solid agar based media lacking histidine.

The cDNA can then be purified from these strains, and used to produce and isolate the bait RATH gene-interacting protein using techniques routinely practiced in the art.

In a particular embodiment, a two hybrid system can be utilized to identify G-α and/or G-α-I subunit amino acid sequences which bind to RATH gene product. In such an embodiment, RATH "bait" is used in connection with a library encoding G-α and/or G-α-I subunit fragments. G-α and/or G-α-I subunit sequences are preferably derived from G-α and/or G-α-I subunits present in T cells, and are most preferably derived from T cell-specific G-α and/or G-α-I subunits. G-α and/or G-α-I nucleic acid and amino acid sequences are well known to those of skill in the art (see, e.g., Gilman, A., Ann. Rev. Immun., which is incorporated herein by reference in its entirety).

In another particular embodiment, a two hybrid system can be utilized to identify calpactin amino acid sequences which bind to RATH gene product. In such an embodiment, RATH "bait" is used in connection with a library encoding calpactin fragments. Calpactin nucleic acid and amino acid sequences are well known to those of skill in the art (see, e.g., Waisman, D. A., 1995, Mol. Cell. Biochem. 149/150:301–322, and the references cited therein).

5.4.2.3. ASSAYS FOR COMPOUNDS THAT INTERFERE WITH RATH GENE PRODUCT/INTRACELLULAR MACROMOLECULE INTERACTION

The RATH gene products of the invention may, in vivo, interact with one or more intracellular macromolecules, such as proteins. Such macromolecules may include, but are not limited to, nucleic acid molecules and those proteins identified via methods such as those described, above, in Section 5.4.2.2. For purposes of this discussion, such intracellular macromolecules are referred to herein as "interacting partners". Compounds that disrupt RATH interactions in this way may be useful in regulating the activity of the RATH gene product, including mutant RATH gene products. Such compounds may include, but are not limited to molecules such as peptides, and the like, as described, for example, in Section 5.4.2.1. above, which would be capable of gaining access to the intracellular RATH gene product.

The basic principle of the assay systems used to identify compounds that interfere with the interaction between the RATH gene product and its intracellular interacting partner or partners involves preparing a reaction mixture containing the RATH gene product, and the interacting partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of RATH gene product and its intracellular interacting partner. Control reaction mixtures are incubated without the test compound or with a placebo. The formation of any complexes between the RATH gene protein and the intracellular interacting partner is then detected. The formation of a complex in the control reaction, but not in the reaction mixture containing the test compound, indicates that the compound interferes with the interaction of the RATH gene protein and the interacting partner. Additionally, complex formation within reaction mixtures containing the test compound and normal RATH gene protein may also be compared to complex formation within reaction mixtures containing the test compound and a mutant RATH gene protein. This comparison may be important in those cases wherein it is desirable to identify compounds that disrupt interactions of mutant but not normal RATH gene proteins.

The assay for compounds that interfere with the interaction of the RATH gene products and interacting partners can be conducted in a heterogeneous or homogeneous format. Heterogeneous assays involve anchoring either the RATH gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the RATH gene products and the interacting partners, e.g., by competition, can be identified by conducting the reaction in the presence of the test substance; i.e., by adding the test substance to the reaction mixture prior to or simultaneously with the RATH gene protein and intracellular interacting partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the RATH gene product or the interacting partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the RATH gene product or interacting partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the interacting components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the RATH gene protein and the interacting partner is prepared in which either the RATH gene product or its interacting partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt RATH gene protein/intracellular interacting partner interaction can be identified.

In a particular embodiment, the RATH gene product can be prepared for immobilization using recombinant DNA techniques described in Section 5.1, above. For example, the RATH coding region can be fused to a glutathione-S-transferase (GST) gene using a fusion vector, such as pGEX-5X-1, in such a manner that its interacting activity is maintained in the resulting fusion protein. The intracellular interacting partner can be purified and used to raise a monoclonal antibody, using methods routinely practiced in the art and described above, in Section 5.2. This antibody can be labeled with the radioactive isotope $^{125}$I, for example, by methods routinely practiced in the art. In a heterogeneous assay, e.g., the GST-RATH fusion protein can be anchored to glutathione-agarose beads. The intracellular interacting partner can then be added in the presence or absence of the test compound in a manner that allows interaction, e.g., binding, to occur. At the end of the reaction period, unbound material can be washed away, and the labeled monoclonal antibody can be added to the system and allowed to bind to the complexed components. The interaction between the RATH gene protein and the intracellular interacting partner can be detected by measuring the amount of radioactivity that remains associated with the glutathione-agarose beads. A successful inhibition of the interaction by the test compound will result in a decrease in measured radioactivity.

Alternatively, the GST-RATH gene fusion protein and the intracellular interacting partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the RATH gene product/interacting partner interaction can be detected by adding the labeled antibody and measuring the radioactivity associated with the beads.

In a particular embodiment, one interacting partner is a RATH gene product sequence and the second interacting partner is a G-$\alpha$-I subunit or the portion of the subunit which binds RATH. Test compounds identified via such an embodiment represent a compound which inhibits RATH/G-$\alpha$-I subunit complex formation.

In another particular embodiment, one interacting partner is a RATH gene product sequence and the second interactng partner is a calpactin molecule or a RATH gene product-binding portion of a calpactin molecule. Test compounds identified via such an embodiment represent a compound which inhibits RATH/calpactin complex formation.

In another embodiment of the invention, these same techniques can be employed using peptide fragments that correspond to the binding domains of the RATH protein and/or the intracellular interacting partner, in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interacting, e.g., binding. Alternatively, one protein can be anchored to a solid surface using methods described in this Section above, and allowed to interact with, e.g., bind, to its labeled interacting partner, which has been treated with a proteolytic enzyme, such as trypsin. After washing, a short, labeled peptide comprising the interacting, e.g., binding, domain may remain associated with the solid material, which can be isolated and identified by amino acid sequencing. Also, once the gene coding for the intracellular binding partner is obtained, short gene segments can be engineered to express peptide fragments of the protein, which can then be tested for binding activity and purified or synthesized.

For example, and not by way of limitation, a RATH gene product can be anchored to a solid material as described, above, in this Section by making a GST-RATH fusion protein and allowing it to bind to glutathione agarose beads. The interactive intracellular binding partner can be labeled with a radioactive isotope, such as $^{35}S$, and cleaved with a proteolytic enzyme such as trypsin. Cleavage products can then be added to the anchored GST-RATH fusion protein and allowed to bind. After washing away unbound peptides, labeled bound material, representing the intracellular interacting partner binding domain, can be eluted, purified, and analyzed for amino acid sequence by well-known methods. Peptides so identified can be produced synthetically or fused to appropriate facilitative proteins using recombinant DNA technology.

In another embodiment, a two-hybrid screening assay could be used to identify drugs that block the interaction between RATH and the G-α-1 subunit. This strategy would employ a two-hybrid containing yeast strain whose growth on synthetic complete medium lacking L-histidine is conditional on the physical interaction between RATH and its cognate G-α-1 subunit. In one example of such an embodiment, the strain would be spread in a thin lawn on a plate made of synthetic complete medium lacking L-histidine. Filter disks containing test compounds would be applied to the plates. Most test compounds would not affect the interaction between RATH and its cognate G-α-1 subunit and consequently a confluent lawn of yeast would grow around the disks impregnated with such compounds. Test compounds that inhibit the interaction between RATH and its cognate G-α-1 subunit would block growth of the yeast strain around the filter disks containing them causing zones of growth inhibition. Those compounds could then be tested against wild-type yeast to confirm that they are not simply fungistatic or fungicidal. Such an embodiment can also be performed in liquid culture, utilizing standard well known methods for measuring cell growth in culture.

In a variation of such an embodiment, the test compound can comprise portions of the G-α or G-α-I subunit such that by identifying inhibitory peptides the method identifies the portion of the subunit which interacts with the RATH gene product.

In yet another embodiment, a two-hybrid screening assay could be used to identify drugs that block the interaction between RATH and calpactin. This strategy would employ a two-hybrid containing yeast strain whose growth on synthetic complete medium lacking L-histidine is conditional on the physical interaction between RATH and its cognate calpactin-binding portion. In one example of such an embodiment, the strain would be spread in a thin lawn on a plate made of synthetic complete medium lacking L-histidine. Filter disks containing test compounds would be applied to the plates. Most test compounds would not affect the interaction between RATH and calpactin and consequently a confluent lawn of yeast would grow around the disks impregnated with such compounds. Test compounds that inhibit the interaction between RATH and its cognate calpactin would block growth of the yeast strain around the filter disks containing them causing zones of growth inhibition. Those compounds could then be tested against wild-type yeast to confirm that they are not simply fungistatic or fungicidal. Such an embodiment can also be performed in liquid culture, utilizing standard well known methods for measuring cell growth in culture.

In a variation of such an embodiment, the test compound can comprise portions of the calpactin molecule such that by identifying inhibitory peptides the method identifies the portion of calpactin which interacts with the RATH gene product.

5.4.2.4. CELL-BASED ASSAYS FOR IDENTIFICATION OF COMPOUNDS WHICH MODULATE RATH ACTIVITY

Cell-based methods are presented herein which identify compounds capable of treating immune disorders and/or modulating RATH-mediated signal transduction events and cellular processes by modulating RATH activity. Specifically, such assays identify compounds which affect RATH-dependent G-protein-mediated signal transduction processes. Compounds identified via such methods can, for example, be utilized in methods for treating immune disorders involving T cell, including TH cell and TH cell subpopulation, activity, such as T cell activation.

In one embodiment, the cell-based assays are yeast-based assays comprising yeast cells containing an RATH gene sequence which expresses RATH gene product in the yeast cell. In yeast, RATH, as an RGS family member, modulates signal transduction induced through the phermone-response pathway. In some instances, such modulation represents a "blunting" or desensitization of the signal transduction pathway to external stimulus, e.g., in the case of yeast, a factor mating phermone. Such modulation can easily be scored for in a number of ways (see, e.g., Weiner, J. L. et al., 1993, J. Biol. Chem. 268:8070–8077, which is incorporated herein by reference in its entirety) and can be utilized to identify compounds which modulate RATH activity. That is, such yeast cell-based assays can easily identify test compounds which affect RATH's modulation of signal transduction pathways.

Yeast cells utilized in such assays contain RATH gene sequences, such as those described in Section 5.1 above, capable of being expressed in the yeast cells. The yeast cells can be, for example, mutant yeast cells which are supersensitive to mating phermone, e.g., sst2 loss-of-function mutants such as, for example, sst2 deletion mutants (sst2Δ). Alternatively, wild type yeast cells containing RATH gene sequences capable of being expressed in the yeast cells can be utilized in the assays. Techniques for expressing gene sequences in such yeast cells are well known to those of skill in the art.

Sensitivity of yeast cells to phermone in the presence or absence of test compound can, for example, be tested via the use of growth-arrest (halo) assays. These growth-arrest assays comprise lawns of yeast cells exposed to phermone disks containing increasing levels of yeast phermone. Phermone sensitivity can be assayed by measuring the clear zone which develops around the disks, representing an area of growth inhibition. RATH-containing yeast cells exhibit a decreased sensitivity to phermone and, therefore, the clear zone area around phermone disks should be smaller than that formed by the same type of yeast cells which do not contain RATH.

An assay for identifying compounds which modulate RATH activity can comprise contacting RATH-containing yeast cells as described above with phermone and a test compound for a time sufficient to form a yeast cell lawn, at which time the clear zone area around the phermone source is measured. If the clear zone area differs from the clear zone area surrounding phermone of the same concentration within a lawn produced by the same type of yeast cells in the absence of test compound, then the test compound modulates RATH activity and is a candidate for the treatment of immune disorders.

As a control, a cell of the same yeast type but not containing RATH is exposed to phermone and test compound, in order to identify and discard non RATH-specific modulators.

In instances where the modulatory test compound produces an increase in the clear zone, the test compound inhibits or suppresses RATH activity. In instances where the modulatory test compound produces a decrease in the clear zone, the test compound increases or enhances RATH activity. Depending on the individual immune disorder, either of these two types of modulatory compounds could be utilized as part of a method of treatment.

In an alternative embodiment, yeast cells as described above further containing a phermone-inducible reporter gene can be utilized to identify test compounds which modulate RATH activity. Such phermone-inducible reporter genes are well known to those of skill in the art and can include, for example, a calorimetric reporter sequence e.g., lacZ, whose expression is phermone-inducible (see, e.g., Druey, K. M. et al., 1996, Nature 379:742–746).

In such an assay, the yeast cells are contacted with test compound and phermone. Reporter gene expression in the presence of phermone is measured in the presence and absence of test compound. If reporter gene expression in the presence of test compound differs, the test compound modulates RATH activity and is a candidate for the treatment of immune disorders.

As a control, a cell of the same yeast type but not containing RATH is exposed to phermone and test compound, in order to identify and discard non RATH-specific modulators.

In instances where the modulatory test compound produces an increase in reporter gene expression, the test compound inhibits or suppresses RATH activity. In instances where the modulatory test compound produces a decrease in reporter gene expression, the test compound increases or enhances RATH activity. Depending on the individual immune disorder, either of these two types of modulatory compounds could be utilized as part of a method of treatment.

In an alternate embodiment, expression cloning of mammalian G-protein coupled receptor pathway inhibitors may be carried out in yeast cells containing a RATH gene sequence which expresses RATH gene product in the yeast cell. Binding of mating phermone such as alpha-factor to its receptor arrests cell growth. A MATa yeast strain that expresses the alpha factor receptor can be transformed with a library of murine or human cDNAs cloned in a yeast expression vector. Yeast transformants are then plated on a growth medium that selects for transformants and contains a concentration of mating phermone known to inhibit the growth of wild-type yeast cells. Transformants that are able to grow are isolated, and the library plasmid that they contain, is isolated. In order to eliminate false positives, isolated plasmids are reintroduced into the original MATa strain and the above screen is repeated. Those yeast cells that are able to grow contain a plasmid able to confer resistance to mating phermone on the host strain. cDNAs isolated in this fashion are sequenced and biologically characterized.

In another embodiment, assays such as MAP kinase assays as described in Section 7, below can be utilized to identify compounds that affect RATH activity. For example, such assays could identify compounds which modulate (either agonize or antagonize) the ability of RATH to "blunt" signaling via signal transduction, such as G-protein mediated signal transduction, events.

In yet another embodiment, assays such as GAP kinase assays as described in Section 7, below can be utilized to identify compounds that affect RATH activity. For example, such assays could identify compounds which modulate (either agonize or antagonize) the ability of RATH to accelerate the intrinsic rate of GDP replacement of GTP on G-α subunits of G proteins.

In another embodiment, assays such as the cell adhesion assays described in Section 8, below, can be utilized to identify compounds that modulate (antagonize or agonize) the ability of RATH to regulate integrin-coupled cell adhesion events.

In addition, assays can be utilized that identify compounds that modulate the expression of the RATH genes. For example, such methods can identify compounds that affect the up or down regulation of RATH in response to extracellular signalling events, such as cellular activation events. Such assays can include ones that measure RATH mRNA or protein levels in response to activation signals such as, for example, T cell activation signals.

5.5. METHODS FOR THE AMELIORATION OF T CELL DISORDER SYMPTOMS

Described below are methods and compositions for treating immune disorders and immune disorder symptoms. Such immune disorders can include, but are not limited to, chronic inflammatory diseases and disorders, such as Crohn's disease, reactive arthritis, including Lyme disease, insulin-dependent diabetes, organ-specific autoimmunity, including multiple sclerosis, rheumatoid arthritis, inflammatory bowel disease, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helmininthic (e.g., leishmaniasis) and certain viral infections, including HIV, and bacterial infections, including tuberculosis and lepromatous leprosy.

Such methods can also be utilized for treatment or modulation of any disorder or cellular process that is mediated or regulated by RATH gene product function. That is RATH-mediated signal transduction, including, but not limited to, G-protein-mediated signal transduction, events can be modulated via the methods described herein. Further, RATH effector functions such as integrin-coupled cell adhesion can be modulated via such methods, as can the ability of RATH to interact with, for example, calpactin, a molecule known to influence a number of important cellular processes.

Such methods comprise methods which modulate RATH gene and gene product activity. In certain instances the treatment will require an increase, upregulation or activation of RATH activity, while in other instances, the treatment will require a decrease, downregulation or suppression of RATH activity. "Increase" and "decrease" refer to the differential level of RATH activity relative to RATH activity in the cell type of interest in the absence of modulatory treatment. Methods for the decrease of RATH activity are discussed in Section 5.5.1, below. Methods for the increase of RATH activity are discussed in Section 5.5.2, below. Methods which can either increase or decrease RATH activity depending on the particular manner in which the method is practiced are discussed in Section 5.5.3, below.

5.5.1 METHODS FOR DECREASING RATH ACTIVITY

As discussed, above, successful treatment of certain immune disorders can be brought about by techniques which serve to decrease RATH activity. Activity can be decreased by, for example, directly decreasing RATH gene product activity and/or by decreasing the level of RATH gene expression.

For example, compounds such as those identified through assays described, above, in Section 5.4, above, which decrease RATH activity can be used in accordance with the invention to ameliorate symptoms associated with such immune disorders. As discussed in Section 5.4, above, such molecules can include, but are not limited to peptides, including soluble peptides, and small organic or inorganic molecules, and can be referred to as RATH antagonists. Techniques for the determination of effective doses and administration of such compounds are described, below, in Section 5.6.

Further, antisense and ribozyme molecules which inhibit RATH gene expression can also be used in accordance with the invention to reduce the level of RATH gene expression, thus effectively reducing the level of RATH gene product present, thereby decreasing the level of RATH activity. Still further, triple helix molecules can be utilized in reducing the level of RATH gene activity. Such molecules can be designed to reduce or inhibit either wild type, or if appropriate, mutant target gene activity. Techniques for the production and use of such molecules are well known to those of skill in the art.

Antisense approaches involve the design of oligonucleotides (either DNA or RNA) that are complementary to RATH gene RNA. The antisense oligonucleotides will bind to the complementary RATH gene mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. See generally, Wagner, R., 1994, Nature 372:333–335. Thus, oligonucleotides complementary to either the 5'- or 3'- non-translated, non-coding regions of the RATH gene, as shown, for example, in FIGS. 1A–1C, could be used in an antisense approach to inhibit translation of endogenous RATH gene mRNA.

Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of target or pathway gene mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

The antisense molecules should be delivered to cells which express the RATH gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous RATH gene transcripts and thereby prevent translation of the RATH gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chamboh, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–15 1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue.

Ribozymes are enzymatic RNA molecules capable of catalyzing the specific cleavage of RNA (For a review see, for example Rossi, J., 1994, Current Biology 4:469–471). The mechanism of ribozyme action involves sequence specific hybridization of the ribozyme molecule to complementary target RNA, followed by a endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding target gene proteins.

Ribozyme molecules designed to catalytically cleave RATH gene mRNA transcripts can also be used to prevent translation of RATH gene mRNA and expression of target or pathway gene. (See, e.g., PCT International Publication WO90/11364, published Oct. 4, 1990; Sarver et al., 1990, Science 247:1222–1225). While ribozymes that cleave mRNA at site specific recognition sequences can be used to destroy RATH gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. Preferably the ribozyme is engineered so that the cleavage recognition site is located near the 5' end of the RATH gene mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in an RATH gene.

As in the antisense approach, the ribozymes can be composed of modified oligonucleotides (e.g. for improved stability, targeting, etc.) and should be delivered to cells which express the RATH gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous RATH gene messages and inhibit translation. Because ribozymes unlike antisense molecules, are catalytic, a lower intracellular concentration is required for efficiency.

In instances wherein the antisense, ribozyme, and/or triple helix molecules described herein are utilized to inhibit mutant gene expression, it is possible that the technique can also efficiently reduce or inhibit the transcription (triple helix) and/or translation (antisense, ribozyme) of mRNA produced by normal target gene alleles that the possibility can arise wherein the concentration of normal target gene product present can be lower than is necessary for a normal phenotype. In such cases, to ensure that substantially normal levels of target gene activity are maintained, therefore, nucleic acid molecules that encode and express target gene polypeptides exhibiting normal target gene activity can be introduced into cells via gene therapy methods that do not contain sequences susceptible to whatever antisense, ribozyme, or triple helix treatments are being utilized. Alternatively, in instances whereby the target gene encodes an extracellular protein, it can be preferable to coadminister normal target gene protein in order to maintain the requisite level of target gene activity.

Anti-sense RNA and DNA, ribozyme, and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules can be introduced as a means of increasing intracellular stability and half-life. Possible modifications include, but are not limited to, the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

Endogenous RATH gene expression can also be reduced by inactivating or "knocking out" the target and/or pathway gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional RATH gene (or a completely unrelated DNA sequence) flanked by DNA homologous to the endogenous RATH gene (either the coding regions or regulatory regions of the RATH gene) can be used, with or without a selectable marker and/or a negative selectable marker, to transfect cells that express RATH gene in vivo. Insertion of the DNA construct, via targeted homologous recombination, results in inactivation of the RATH gene. Such approaches are particularly suited in the agricultural field where modifications to ES (embryonic stem) cells can be used to generate animal offspring with an inactive RATH gene (e.g., see Thomas & Capecchi 1987 and Thompson 1989, supra). Such techniques can also be utilized to generate immune disorder animal models. It should be noted that this approach can be adapted for use in humans provided the recombinant DNA constructs are directly administered or targeted to the required site in vivo using appropriate viral vectors, e.g., herpes virus vectors.

Alternatively, endogenous RATH gene expression can be reduced by targeting deoxyribonucleotide sequences complementary to the regulatory region of the RATH gene (i.e., the RATH gene promoter and/or enhancers) to form triple helical structures that prevent transcription of the RATH gene in target cells in the body. (See generally, Helene, C. 1991, Anticancer Drug Des., 6(6):569–84; Helene, C., et al., 1992, Ann, N.Y. Accad. Sci., 660:27–36; and Maher, L. J., 1992, Bioassays 14(12):807–15).

5.5.2. POSITIVE MODULATORY TECHNIQUES

As discussed above, successful treatment of certain immune disorders can be brought about by techniques which serve to increase the level of RATH activity. Activity can be increased by, for example, directly increasing RATH gene product activity and/or by increasing the level of RATH gene expression.

For example, compounds such as those identified through assays described, above, in Section 5.4, which increase RATH activity can be used in accordance with the invention to treat immune disorders and immune disorder symptoms. As discussed in Section 5.4, above, such molecules can include, but are not limited to peptides, including soluble peptides, and small organic or inorganic molecules, and can be referred to as RATH antagonists.

For example, a compound can, at a level sufficient to treat immune disorder and symptoms, be administered to a patient exhibiting such symptoms. Any of the techniques discussed, below, in Section 5.6, can be utilized for such administration. One of skill in the art will readily know how to determine the concentration of effective, non-toxic doses of the compound, utilizing techniques such as those described, below, in Section 5.6.1.

In instances wherein the compound to be administered is a peptide compound, DNA sequences encoding the peptide compound can be directly administered to a patient exhibiting immune disorder symptoms, at a concentration sufficient to produce a level of peptide compound sufficient to ameliorate symptoms of an immune disorder, for example, multiple sclerosis. Any of the techniques discussed, below, in Section 5.6, which achieve intracellular administration of compounds, such as, for example, liposome administration, can be utilized for the administration of such DNA molecules. The DNA molecules can be produced, for example, by well known recombinant techniques.

In the case of peptides compounds which act extracellularly, the DNA molecules encoding such peptides can be taken up and expressed by any cell type, so long as a sufficient circulating concentration of peptide results for the elicitation of a reduction in the immune disorder symptoms. In the case of compounds which act intracellularly, the DNA molecules encoding such peptides must be taken up and expressed by the T cell population of interest at a sufficient level to bring about the reduction of immune disorders.

Any technique which serves to selectively administer DNA molecules to the T cell population of interest is, therefore, preferred, for the DNA molecules encoding intracellularly acting peptides, via, for example a delivery complex.

Such a delivery complex can comprise an appropriate nucleic acid molecule and a targeting means. Such targeting means can comprise, for example, sterols lipids, viruses or target cell specific binding agents. Viral vectors can include, but are not limited to adenovirus, adeno-associated virus, and retrovirus vectors, in addition to other particles that introduce DNA into cells, such as liposomes. In the case of asthma, for example, techniques for the selective administration of the molecules to T cell subpopulations residing within lung tissue are preferred.

Further, in instances wherein the TH cell subpopulation-related disorder involves an aberrant RATH gene, patients can be treated by gene replacement therapy. One or more copies of a normal RATH gene or a portion of the gene that directs the production of a normal RATH gene protein with RATH gene function, can be inserted into cells, via, for example a delivery complex.

Such a delivery complex can comprise an appropriate nucleic acid molecule and a targeting means. Such targeting means can comprise, for example, sterols lipids, viruses or target cell specific binding agents. Viral vectors can include, but are not limited to adenovirus, adeno-associated virus, and retrovirus vectors, in addition to other particles that introduce DNA into cells, such as liposomes. For example, such RATH gene sequences can encode peptide sequences which comprise the RATH RGS domain contained within the amino acid sequence depicted in FIGS. 1A–1C (SEQ ID NO:2). Such gene replacement techniques can be accomplished either in vivo or in vitro. As the RATH gene encodes a gene product which acts intracellularly, the gene must be expressed with the T cell population of interest. Techniques which select for expression within the cell type of interest are, therefore, preferred. In vivo, such techniques can, for example, include appropriate local administration of RATH gene sequences.

Additional methods which may be utilized to increase the overall level of RATH activity include the introduction of appropriate RATH gene-expressing cells, preferably autologous cells, into a patient at positions and in numbers which are sufficient to ameliorate the symptoms of the immune disorder of interest. Such cells may be either recombinant or non-recombinant. Among the cells which can be administered to increase the overall level of RATH gene expression in a patient are normal cells, which express the RATH gene. The cells can be administered at the anatomical site of expression, or as part of a tissue graft located at a different site in the body. Such cell-based gene therapy techniques are well known to those skilled in the art, see, e.g., Anderson, et al., U.S. Pat. No. 5,399,349; Mulligan & Wilson, U.S. Pat. No. 5,460,959.

In vitro, RATH gene sequences can be introduced into autologous cells. These cells expressing the RATH gene sequence of interest can then be reintroduced, preferably by intravenous administration, into the patient until the disorder is treated and symptoms of the disorder are ameliorated.

5.5.3 ADDITIONAL MODULATORY TECHNIQUES

Described herein are modulatory techniques which, depending on the specific application for which they are utilized, can yield either increase or decrease RATH activity levels leading to the amelioration of immune disorders such as those described above.

Antibodies exhibiting modulatory capability can be utilized to ameliorate immune disorders. Depending on the specific antibody, the modulatory effect can be increase or decrease RATH activity. Such antibodies can be generated using standard techniques described in Section 5.3, above, against full length wild type or mutant RATH proteins, or against peptides corresponding to portions of the proteins. The antibodies include but are not limited to polyclonal, monoclonal, FAb fragments, single chain antibodies, chimeric antibodies, and the like.

Because RATH is an intracellular protein, it is preferred internalizing antibodies be used. However, lipofectin or liposomes can be used to deliver the antibody or a fragment of the Fab region which binds to the RATH gene product epitope into cells. Where fragments of the antibody are used, the smallest inhibitory fragment which binds to the RATH protein's binding domain is preferred. For example, peptides having an amino acid sequence corresponding to the domain of the variable region of the antibody that binds to the RATH protein can be used. Such peptides can be synthesized chemically or produced via recombinant DNA technology using methods well known in the art (e.g., see Creighton, 1983, supra; and Sambrook et al., 1989, above). Alternatively, single chain antibodies, such as neutralizing antibodies, which bind to intracellular epitopes can also be administered. Such single chain antibodies can be administered, for example, by expressing nucleotide sequences encoding single-chain antibodies within the target cell population by utilizing, for example, techniques such as those described in Marasco et al. (Marasco, W. et al., 1993, Proc. Natl. Acad. Sci. USA 90:7889–7893).

5.6. PHARMACEUTICAL PREPARATIONS AND METHODS OF ADMINISTRATION

The compounds and nucleic acid sequences described herein can be administered to a patient at therapeutically effective doses to treat or ameliorate immune disorders, e.g., TH cell-related disorders. A therapeutically effective dose refers to that amount of a compound or TH cell population sufficient to result in amelioration of the immune disorder symptoms, or alternatively, to that amount of a nucleic acid sequence sufficient to express a concentration of RATH gene product which results in the amelioration of the immune disorder symptoms.

5.6.1. EFFECTIVE DOSE

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

5.6.2. FORMULATIONS AND USE

Pharmaceutical compositions for use in accordance with the present invention can be formulated in conventional manner using one or more physiologically acceptable carriers or excipients.

Thus, the compounds and their physiologically acceptable salts and solvents can be formulated for administration by inhalation or insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.c. gelatin for use in an inhaler or insufflator can be formulated containing a powder mix of the compound and a suitable powder base such as lactose or starch.

The compounds can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use. It is preferred that the TH cell subpopulation cells be introduced into patients via intravenous administration.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

6. EXAMPLE

IDENTIFICATION OF A NOVEL GENE FAMILY (RATH) INVOLVED IN T CELL ACTIVITY

Described herein is the identification and characterization of a novel gene family referred to as the RATH gene family. Members of the RATH gene family contain RGS ("regulator of G-protein signalling") domains, exhibit a T cell, TH cell or TH cell subpopulation specific or enhanced expression pattern, and can be involved in modulation of T cell activity, such as T cell activation. The identification, characterization of an exemplary RATH gene family member, termed RATH1.1, is described below.

6.1. PARADIGMS FOR THE IDENTIFICATION OF GENES DIFFERENTIALLY EXPRESSED GENES IN TH CELL SUBPOPULATIONS

The differential display technique is a procedure, utilizing the well-known polymerase chain reaction (PCR; the experimental embodiment set forth in Mullis, K. B., 1987, U.S. Pat. No. 4,683,202), which allows for the identification of sequences derived from genes which are differentially expressed. As described below in Section 6.2, such a technique was utilized for the identification of gene sequences which are involved in immune disorder states, e.g., TH cell subpopulation-related disorder states, and/or which are involved in differentiation, maintenance and/or effector function of TH cell subpopulations.

Briefly, TH cell subpopulations activated with appropriate antigens after which the expression patterns of, e.g. TH1 vs. TH2 and/or activated vs. non-activated cells were analyzed. As described in detail in Section 6.2, activated and non-activated TH1 and TH2 cell lines were analyzed according to such a method.

After stimulation, RNA is isolated and reverse-transcribed into single-stranded cDNA, utilizing standard techniques which are well known to those of skill in the art. Next, pairs of PCR primers, as described below, which allow for the quantitative amplification of clones representing a reproducible subset of the RNA transcripts present within any given cell. Utilizing different pairs of primers allows each of the primed mRNA transcripts present in a cell to be amplified. Among such amplified transcripts can be identified those which have been produced from differentially expressed genes.

The pattern of clones resulting from the reverse transcription and amplification of the mRNA of two different cell types is displayed and compared via sequencing gel electrophoresis. Differentially expressed genes are indicated by differences in the two banding patterns. Once identified the band can be purified and used as a probe to screen a library for full length cDNA clones. Such a technique was successfully utilized, as described below, to identify the RATH 1.1 gene.

6.2 ISOLATION OF AN INDUCIBLE TH1 SPECIFIC GENE SEQUENCE

The section below describes the identification of a novel gene sequence differentially expressed in a TH1-specific manner.

6.2.1 STIMULATION, CELL CULTURE AND PREPARATION OF TH1 AND TH2 RNA

To identify gene sequences differentially expressed in TH cell subpopulations, the differential display technique, described above, in Section 6.1, was utilized. TH1 and TH2 clonal cell lines were stimulated, and RNA from the cell lines was isolated. Two TH1 (D1.1 and Dorris) and two TH2 (Dax and CDC25) cell lines were utilized.

For normal culture, T-helper cells were stimulated every 10–14 days with freshly isolated MHC-matched antigen presenting cells, in combination with specific antigen (D1.1: Rabbit Gamma Globulin, Sigma; Dorris: HEL lysozyme, Sigma; Dax: Hel lysozyme, Sigma; CDC25: Rabbit Gamma Globulin, Sigma). Further, cultures were fed every 2–3 days with fresh IL-2 (Boehringer Mannheim). Cells were cultured according to standard protocols (Coligan, et al., eds., 1995, Current Protocols in Immunology, John Wiley & Sons, Inc.).

Prior to stimulation, cells were starved of both antigen (at least 10 days) and IL-2 (2–3 days), and viable cells were purified with Lymphocyte Separation Medium (Organon Teknika). Cells were separated into two groups. One group was left unstimulated. One group was stimulated for 6 hours by plating on plastic culture dishes which had been coated with anti-mouse CD3 epsilon monoclonal antibody (hybridoma supernatent from the 145–2C11 hybridoma; Parmingen, Inc., San Diego Calif.) at 1.5 µg/ml in PBS for one hour at 370° C.

Total cellular RNA was isolated from the cells of each group (unstimulated or anti-CD3 stimulated) as follows. Specifically, cells were quick frozen on dry ice, homogenized together with a mortar and pestle under liquid nitrogen and total cellular RNA was extracted from cells with RNAzol™ (TEL-TEST, Inc., Friendswood TX) according to the manufacturer's instructions. Briefly, the cells were solubilized in an appropriate amount of RNAzol™ and RNA was extracted by the addition of 1/10 v/v chloroform to the solubilized sample followed by vigorous shaking for approximately 15 seconds. The mixture was then centrifuged for 15 minutes at 12,000 g and the aqueous phase was removed to a fresh tube. RNA was precipitated with isopropanol. The resultant RNA pellet was dissolved in water and re-extracted with an equal volume of chloroform to remove any remaining phenol. The extracted volume was precipitated with 2 volumes of ethanol in the presence of 150 mM sodium acetate. The precipitated RNA was dissolved in water and the concentration determined spectroscopically ($A_{260}$).

Residual DNA was removed by digesting for 30 min at 370° C. with RNAse free DNAse I (Boehringer Mannheim). After extraction with phenol/chloroform and ethanol precipitation, the RNA was dissolved in DEPC (diethyl pyrocarbonate)-treated water.

RNA populations from the two different stimulated and unstimulated TH1 and TH2 cell lines were compared using the Delta RNA Fingerprinting Kit (Clontech #PT1173–1), according to the manufacturer's protocol.

6.2.2 IDENTIFICATION OF A TH1 SPECIFIC GENE SEQUENCE

The RNA isolated for TH1 and TH2 cells, as described, above, in Section 6.2.1., was quantitatively amplified and the cells' gene expression patterns were analyzed as described herein. The analysis yielded an approximately 220 bp differentially expressed cDNA gene sequence which, interestingly, was expressed exclusively in the two TH1 clones examined, but was absent in non-stimulated TH1 clones and in all the TH2 clones examined.

Specifically, cDNA synthesis was performed using DNA-free RNA (above) from 2 independent TH1 clones and 2 independent TH2 clones. For each sample, cDNA synthesis was performed using 2 µg of total RNA and 1 µl of oligo dT primer (1 µM), as described in the manufacturer's protocol. cDNA samples were stored at –20° C., and used for PCR amplification using various combinations of the following 25 bp 5' (P primers) and 30 bp 3' (T primers):

P: 5'-ATTAACCCTCACTAAATGCTGGGTG-3' (SEQ ID NO:5) (forward primer) and

T: 5'-CATTATGCTGAGTGATATCTTTTTTTTTAA-3' (SEQ ID NO:6) (reverse primer).

PCR amplification was performed according to the provided protocol, using the CLONTECH Advantage cDNA PCR Core Kit (K1905-1). Three low stringency PCR cycles (annealing temp. 40° C.) were followed by 22–25 high stringency PCR cycles (annealing temp. 60° C.), and PCR products were separated by denaturing PAGE using 5% polyacrylamide/8M urea gels, and PCR products were visualized by autoradiography. Differentially expressed bands were excised from dried gels and re-amplified using the original primers. Re-amplified products were cloned into pCR 2.1, using the TA Cloning Kit (Invitrogen), and individual isolates were sequenced.

6.3 CLONING AND CHARACTERIZATION OF RATH1.1, A NOVEL TH1-SPECIFIC GENE

The subsection below describes the isolation and characterization of a gene, termed the RATH1.1 gene. The RATH1.1 gene was obtained by screening of a TH1-specific cDNA library with the 220bp cDNA fragment described above, in Section 6.2. Sequence analysis reveals that RATH1.1 is a novel gene encoding a product which contains an RGS domain. Expression analysis confirms that RATH1.1 represents a TH1-specific gene, and can be involved in T cell activity. RATH1.1 appears to represent a member of a novel gene family, termed the RATH gene family, whose members contain RGS domains, are expressed in a T cell-restricted manner and can be involved in T cell activity such as, for example, T cell activation.

6.3.1 PREPARATION AND SCREENING OF TH-1 SPECIFIC LIBRARY

A TH1-specific cDNA library was screened in an attempt to obtain the full-length sequence corresponding to the 220 bp sequence identified in Section 6.2, above. A TH1-specific cDNA library was generated using polyA+ RNA isolated from the TH1 cell line Dorris (anti-CD3 stimulated), using the Fast Track 2.0 Kit (Invitrogen). cDNA was generated using oligo dT primers and cloned into lambda ZIPLOX phage arms (GIBCO BRL 15394–018), using the Sal I and Not I cloning sites.

The TH-1 specific phage library was screened using a labeled probe generated from the re-amplified 220 bp fragment obtained by the differential display method described above in Section 6.2. Briefly, plaques were screened with the probe overnight at 65° C. in Church's buffer (7% SDS, 250 mM $NaHPO_4$, 3 µM EDTA, 1% BSA). The next day, filters were washed in 2×SSC/1% SDS for 30 minutes at 50° C. Positive plaques were rescreened under the same conditions.

The largest positive clone obtained was 2278 bp, and contained one complete open reading frame, which codes for a 201 amino acid having a predicted molecular weight of 22.6 kD. The gene/protein is now referred to as RATH1.1. The RATH1.1 nucleotide and amino acid sequences are depicted in FIGS. 1A–1C.

Comparison of the RATH1.1 sequence to known genes (Altschul, S. F. et al., 1990, J. Mol. Biol. 215:403–410 indicates that RATH1.1 is a novel member of the RGS (regulator of G-protein signalling) family, a gene family thought to encode products involved in G protein-mediated signal transduction (see, e.g., Druey, K. M. et al., 1996, Nature 379:742–746). For example, RATH1.1 exhibits approximately 50% identity and 70% similarity to the RGS4 gene product. The RGS domain is located from approximately amino acid residue 60 to amino acid residue 179 of the RATH1.1 amino acid sequence shown in FIG. 1. Conserved amino acid residues within the RGS region are identified as discussed in the legend to FIGS. 1A–1C.

6.3.2. EXPRESSION OF RATH GENES

Northern blot analysis was carried out to determine the size of the RATH1.1 transcript and the tissue distribution of RATH1.1 expression. As described below, the expression analysis confirmed the TH1-specific RATH1.1 gene expression pattern and, further, revealed that the gene produces a transcript of approximately 3kb.

For northern analysis of murine tissues, total cellular RNA from various murine tissues (spleen, thymus, lymph node, muscle, heart, liver, kidney, brain, uterus and testes) was isolated using the RNA purification techniques as described above in Section 6.2. Cell lines tested included the following: WEHI-3B myelomonocyte, Pu5–1.8 myelomonocyte, P388D1 monocyte-macrophage, IC-21 macrophage, AKR.G2 thyoma, BaF3 pro B-cell, EL-4 lymphoma, NFS-1.0 C.-1 B-cell lymphoma, SOT embryonic fibroblast, EOMA endothelial and BMS-12 bone marrow.

Stimulated and unstimulated TH1 clones D1.1, Dorris and AE7, and TH2 clones D10.G4, DAX and CDC25 were also tested. The TH-1 and TH-2 clones were cultured and stimulated as described above in Section 6.2.1.

RNA samples were electrophoresed in a denaturing agarose gel containing 1–1.5% agarose (SeaKem™ LE, FMC BioProducts, Rockland, Me.) containing 3% formaldehyde. For northern analysis of hematopoietic cell lines, a total of approximately 20 $\mu$g of total RNA was loaded per lane, for all other cell lines approximately 15 $\mu$g of total RNA was loaded per lane. Samples containing the indicated amounts of total RNA were mixed with denaturing loading solution (72% deionized formamide and bromophenol blue) and heated to 70° C. for 5 minutes. Samples were placed on ice and immediately loaded onto gels. Gels were run in 1× MOPS buffer (100 mM MOPS, 25 mM sodium acetate, 5 mM EDTA). After electrophoresis, the gels were stained with ethidium bromide and visualized with ultraviolet light.

After completion of electrophoresis, gels were soaked in 50 mM sodium hydroxide with gentle agitation for approximately 30 minutes to lightly cleave RNA. Gels were rinsed twice in water and then neutralized by soaking in 0.1M Tris-HCl (pH 7.5) for approximately 30 minutes. Gels were briefly equilibrated with 20×SSC (3M sodium chloride, 0.3M sodium citrate) and then transferred to nylon membranes such as Hybond™,-N, (Amersham, Inc., Arlington Heights, Ill.) or Zeta-Probe (Bio-Rad, Inc., Hercules, Calif.) overnight in 20×SSC. Membranes containing transferred RNA were baked at 80° C. for 2 hours to immobilize the RNA.

The 220 bp RATH1.1 probe was prepared as follows. Briefly, 50 ng of purified DNA fragment was used to generate the probe. The fragment was added to a 20 $\mu$l random hexanucleotide labeling reaction (Boehringer Mannhein, Inc., Indianapolis, Ind.) containing random hexamers and a mix of the nucleotides dCTP, dGTP, and dTTP (at a final concentration of 25 $\mu$M each). The reaction mix was heat-denatured at 100° C. for 10 minutes and then chilled on ice. 5 $\mu$l of $\alpha$-$^{32}$P-dATP (50 $\mu$Ci; Amersham, Inc., Arlington Heights, Ill.) and Klenow DNA polymerase (2 units; Boehringer Mannheim, Inc., Indianapolis, Ind) were added. Reactions were incubated at 37° for 30 minutes. Following incubation, 30 $\mu$l water was added to the labeling reaction and unincorporated nucleotides were removed by passing the reactions through a BioSpin-6™ chromatography column (Bio-Rad, Inc., Hercules, Calif.). Specific incorporation was determined using a scintillation counter. 1–5× $10^6$ cpm were used per ml hybridization mixture.

Nylon membranes containing immobilized RNA were prehybridized according to manufacturer's instructions. Radiolabelled probes were heat denatured at 70° C. in 50% deionized formamide for 10 minutes and then added to the hybridization mixture (containing 50% formamide, 10% dextran sulfate, 0.1% SDS, 100 $\mu$g/ml sheared salmon sperm DNA, 5×SSC, 5×Denhardt's solution, 30 mM Tris-HCl (pH 8.5), 50 mM NaPO$_4$ (pH 5) Hybridizations were carried out at 42° C. overnight. Nylon membranes were then bathed for 2 minutes in a wash solution of 0.2×SSC and 0.1% SDS at room temperature to remove most of the remaining hybridization solution. The membranes were then bathed twice in fresh 42° C. preheated wash solution for 20 minutes. Filters were covered in plastic wrap and exposed to autoradiographic film to visualize results.

Northern Blot analyses verify that the RATH1.1 gene is highly upregulated in stimulated TH1 cells. First, northern blot analysis of 3 individual TH1 clones and 3 individual TH2 clones revealed an approximately 3 kb RNA which is highly up-regulated in stimulated TH1 clones, but is absent from all other samples tested.

Consistent with the cell clone data, RATH1.1 message appears to be absent from all of the murine tissues analyzed (i.e., spleen, thymus, lymph node, muscle, heart, liver, kidney, brain, uterus and testes), although the RATH1.1 probe clearly hybridized with itself. Third, northern blot analysis was also performed with a panel of murine hematopoietic cell lines. RNA was obtained from various cell lines which had either been left unstimulated or had been stimulated with appropriate antigen (i.e., either PMA or LPS, as described, above, in Section 1). While RATH1.1 RNA was detected in several of the cell lines tested (Pu51.8, STO, EOMA and BMS12), the expression level was significantly lower than was seen in anti-CD3 stimulated TH1 cells (i.e., only a faint signal was detectable after a 3 day exposure).

6.4. CHROMOSOMAL MAPPING OF THE RATH 1.1 GENE

To determine the chromosomal map position of the RATH1.1 gene the technique of Single Stranded Conformational Polymorphism (SSCP) gel electrophoresis was used. More specifically, the genetic segregation of the Mus sPretus allele of RATH1.1 was followed in 188 backcross progeny of cross (C57B1/6J×Mus spretus) F$_1$ females×C57B1/6J males.

PCR primers were designed from the coding sequence of RATH1.1 cDNA. The following RATH1.1 derived PCR primers were used for amplification of mouse genomic DNA:

5'-AGGCAAGGGGCAGGAAATGAAG-3' (SEQ ID NO:7) (forward primer)

5'-ACTAAATGCTGGGTGGTTGG-3' (SEQ ID NO:8) (reverse primers).

The PCR reaction mixture contained 6 $\mu$l template DNA (10long/$\mu$l), 1.4 $\mu$l 10× Perkin Elmer (Norwalk, Conn.) PCR buffer, 1.12 $\mu$l dNTPs (2.5 mM), 1.05 $\mu$l Forward primer (6 $\mu$M), 1.05 $\mu$l Reverse primer (6 $\mu$M), 0.38 $\mu$l H$_2$O and 3 $\mu$l Amplitaq Hotstart™ polymerase (Perkin Elmer; 0.5U/$\mu$l).

The amplification profile was as follows: 94° C., 2 minutes, at which point the Amplitaq™ was added; then 30 cycles of 94° C., 40 seconds; 55°, 50 seconds; and 72° C., 30 seconds.

Samples were run on both (a) nondenaturing 8% acrylamide gels run at 45 W, room temperature, for 3 hours and (b) nondenaturing 10% acrylamide SSCP (single stranded conformational polymorphism) gels run at 20 W, 4° C., for 2.5 hours. Both types of gels were stained with SYBR Green I and scanned on an MD fluorimager, and gave interpretable results. The primers amplified a 159 bp fragment from C57B1/6J Mus sprettus genomic DNA, consistent with the base pair length between the two primers in the RATH1.1 cDNA.

The segregation pattern of the Mus spretus allele was compared to the segregation pattern of 226 other genetic loci that have been mapped in this backcross panel. By minimizing the number of multiple crossovers between RATH1.1 and other markers it was determined that RATH1.1 maps to murine chromosome 1, 9.8 cM distal of D1MIT12 and 29.2 cM proximal of D1MIT17 (two MIT microsatellite markers; Research Genetics).

6.5 RATH1.1 MODULATES G-PROTEIN MEDIATED SIGNAL TRANSDUCTION

Mutations in the sst2 gene, which encodes an RGS-containing gene product, cause increased sensitivity and defective desensitization to signal transduction induced by alpha factor mating pheromone. The results described below demonstrate complementation of sst2 mutations in yeast by the RATH1.1 protein. Thus, these results prove that RATH1.1 acts to modulate G protein-mediated signal transduction. Functional complementation of an sst2 mutation by RATH1.1 provides a convenient yeast-based bioassay for RATH1.1 function. Such a bioassay can, for example, be used to identify molecules that are agonists or antagonists of RATH1.1.

Plasmids containing the RATH1.1 coding sequence were constructed as follows. The RATH1.1 coding sequence was cloned into yeast expression vectors pYADE4 and pYPGE2. pYADE4 contains the ADH2 promoter and pYPGE2 contains the PGK promoter. On media where glucose is the sole carbon source, such as the media used in this experiment, the PGK promoter is reported to be 17 times stronger than the ADH2 promoter (Brunelli and Pall, 1993, Yeast, 9:1299–1308).

Oligonucleotides D1 (5'-AGC GGA TCC AAA AAA ATG ACC ATG ATT ACG CCA AGC TCT AAT AC-3') (SEQ ID NO:9) and D2 (5'-AGC AAT CGA TGG AGG CTC AAG TGT GTG AAG GCT CAG-3' (SEQ ID NO:10)) were used to amplify the entire predicted 606 base pair coding sequence of RATH1.1 predicted to encode a 201 (plus stop codon) amino acid protein. Restriction endonuclease sites BamHI and ClaI were engineered into the oligonucleotides to allow the cloning of the PCR fragment encoding the RATH1.1 protein into yeast expression vectors pYADE4 and pYPGE2 (Brunelli and Pall, 1993, Yeast, 9:1299–1308). In addition, the sequence AAAAAA was introduced immediately upstream of the initiator ATG codon to promote efficient translation in yeast (Hinnebusch and Liebman, 1991, The Molecular Biology and Cellular Biology of the Yeast Saccharomyces: Genome Dynamics, Protein Synthesis, and Energetics, Cold Spring Harbor Laboratory Press, 627–735). The PCR product coding RATH1.1 was doubly digested with BamHI and ClaI and ligated after agarose gel purification into pYADE4 and pYPGE2 doubly digested with BamHI and ClaI. Ligation reactions were transformed into the DH5α E. coli stain (Gibco BRL catalog). One E. coli clone containing the RATH1.1 coding sequence in pYADE4 was isolated and named pMB135 and one E. coli clone containing the RATH1.1 coding sequence in pYPGE2 was isolated and named pMB136.

Standard yeast media including synthetic complete medium lacking L-tryptophan were prepared and yeast genetic manipulation were performed as described (Sherman, 1991, Meth. Enzymol., 194:3–21). Yeast transformations were performed using standard protocols (Gietz et al., 1992, Nucleic Acids Res., 20:1425. Ito et al, 1983, J. Bacteriol., 153:163–168).

Isogenic SST2$^+$ (MF42) and sst2$^-$ (MF41) strains were transformed with pYADE4, pYPGE2, pMB135, and pMB136. Transformants were selected on synthetic complete medium lacking L-tryptophan. Transformants were picked from each transformation and were used for further experimentation. The transformants were designated as follows:

MF41 transformed with pYADE4 (MF167); MF41 transformed with pYPGE2 (MF168); MF41 transformed with pMB135 (MF169); MF41 transformed with pMB136 (MF170); MF42 transformed with pYADE4 (MF171); MF42 transformed with YPGE2 (MF172); MF42 transformed with pMB135 (MF173); and MF42 transformed with pMB136 (MF174).

The MF41 and MF42 transformants were subjected to desensitization assays. The assays were performed as follows. MF41 and MF42 transformants were grown to saturation overnight in liquid synthetic complete medium lacking L-tryptophan. Each culture was diluted 1:40 into 2 mls of liquid synthetic complete medium lacking L-tryptophan which was added to 2 mls of 1% (wt/vol) agar dissolved in water and warmed to 50° C. The resulting cell suspension was plated on a synthetic complete medium lacking L-tryptophan plate and allowed to solidify. Sterile BBL blank paper ¼ inch disks (BBL Microbiology Systems) were spotted with 10, 1, 0.1, or 0.01 mg of synthetic alpha factor (Sigma) and were arrayed on top of the solidified agar medium. The diameter of the halos of growth arrested cells surrounding the filter disks containing alpha factor were photographed and measured after 24 hours of growth.

The results obtained from the desensitization assays are tabulated in Table 1. 10 µg of alpha factor causes the SST2+ strain transformed with either pYADE4 or pYPGE2 (MY171 and MY172) to have a ≈1.8 cm zone of growth inhibition. 10 µg of alpha factor causes the SST2+ strain expressing RATH1.1 under the control of the ADH2 promoter (MY173) to have a 1.6 cm zone of growth inhibition and the SST2+ strain expressing RATH1.1 under the control of the strong PGK promoter (MY174) to have a no zone of growth inhibition. RATH1.1 expressed from the strong PGK promoter dramatically negatively regulates the pheromone response pathway and in the assay used in this study completely prevents the signal created by 10 µg of alpha factor from being transduced. Because RATH1.1 is an RGS protein and RGS proteins are thought to function as GAPs (GTPase Activating proteins), it is likely the inhibition of pheromone signal transduction caused by high level RATH1.1 expression in yeast is due to RATH1.1 acting as a GAP on the GPA1 protein, the G-protein alpha subunit that is coupled to the alpha factor receptor in yeast.

10 µg of alpha factor causes the sst2– strain transformed with either pYADE4 or pYPGE2 (MY167 and MY168) to have a ≈3.7 cm zone of growth inhibition. 10 µg of alpha factor causes the sst2– strain expressing RATH1.1 under the control of the ADH2 promoter (MY169) to have a 1.8 cm zone of growth inhibition which is similar to the ≈1.8 cm zone of growth inhibition that 10 µg of alpha factor elicits in a SST2+ strain (MY171 and MY172). Consequently RATH1.1 under the control of the ADH2 promoter functionally complements the sst2– mutation. Such complementation of an sst2– mutation by RATH1.1 is strong evidence that RATH1.1 has GAP activity towards GPA1 and more generally towards G-protein alpha subunits.

10 μg of alpha factor causes the sst2– strain expressing RATH1.1 under the control of the strong PGK promoter (MY170) to have no zone of growth inhibition. The experimental results indicate that in the absence of the SST2 protein, the RATH1.1 protein can completely block the transduction of the signal produced by 10 μg of alpha factor and supports the idea that RATH1.1 acts as a GAP on GPA1. This experimental results also indicate that the alpha factor resistance phenotype conferred by RATH1.1 expression plasmids is a function of the level of RATH1.1 expression, i.e., the stronger PGK promoter causes a stronger phenotype than the weaker ADH2 promoter.

TABLE 1

| Strain Name | Amount of alpha factor added to disk | | | |
|---|---|---|---|---|
| | 10 μg | 1 μg | 1 μg | .01 μg |
| MY167 | 3.7 | 2.7 | 1.7 | 1.0 |
| MY168 | 3.8 | 2.7 | 1.7 | 1.0 |
| MY169 | 1.8 | 0.8 | None | None |
| MY170 | None | None | None | None |
| MY171 | 1.8 | 0.9 | None | None |
| MY172 | 1.9 | 0.8 | None | None |
| MY173 | None | None | None | None |
| MY174 | None | None | None | None |

Diameters of growth inhibition zones in cm caused by filter disks impregnated with different quantities of alpha factor are shown, in centimeters, below each alpha factor concentration.

6.6. CLONING OF THE HUMAN RATH1.1 GENE

The human RATH1.1 gene was cloned as described herein. The human RATH1.1 nucleic acid and amino acid sequences are depicted in FIGS. 2A–2B.

For cloning, human RATH1.1 clones were amplified via PCR from various libraries: human fetal brain (Stratagene, La Jolla, Calif.), human liver, (Stragene) and U937 myeloid cells (Clontech, Palo Alto, Calif.). For amplification, the forward primer used was: 5'-ACCATCCTGCCTACTACG-3' (SEQ ID NO:11) and the reverse primer was: 5'-AGAACCTGCTCCCACAC-3' (SEQ ID NO:12). PCR was performed in a Perkin Elmer 9600 thermal cycler for 35 cycles with a denaturing temperature of 94° C. for 30 seconds, annealing temperature of 55° C. for 30 seconds, and extending temperature of 72° for 30 seconds.

The PCR product was run on a 1.2% agarose gel, excised and subcloned into a pCRII vector from the TA cloning Kit (Invitrogen, San Diego, Calif.). Clones were sequenced using standard automated fluorescent dideoxynucleotide sequencing techniques (Applied Biosystems, Inc., Foster City Calif.).

Like the murine RATH1.1 gene product, human RATH1.1 contains neither a recognizable transmembrane domain nor a signal sequence and encodes an intracellular or membrane-associated gene product. The human RATH1.1 gene product encodes a protein of 202 amino acid residues, as shown in FIGS. 2A–2B.

The human RATH1.1 gene product contains an RGS domain at approximately amino acid residue 61 to 180, and more specifically, approximately amino acid residue 69 to approximately 177, and even more specifically approximately amino acid residue 69 to approximately amino acid residue 171, in the RATH1.1 gene product depicted in FIGS. 2A–2B.

7. EXAMPLE

THE RATH1 GENE PRODUCT FUNCTIONS AS A SIGNAL TRANSDUCTION MEDIATOR.

The Example in this Section presents RATH1 functional data that demonstrate that the RATH1 gene product acts as an intracellular mediator of signal transduction events. Briefly, the data presented show, first, that RATH1 accelerates the intrinsic rate of GDP replacement of GTP on the G-α subunit of G proteins. Second, data is presented showing that RATH1 is a functional regulator of G-protein-mediated signalling by demonstrating that RATH1 blunts signalling via Il-8 receptor and M1/M2 receptors. Third, Northern and Western analyses are presented that demonstrate that stimulation of specific cell lines brings about a stimulation of RATH1 gene expression.

7.1. Materials and Methods

GAP assays: GAP assays were performed as described in Berman et al., 1996, J. Biol. Chem. 271:27209–27212; and Berman et al., 1996, Cell 86:445–452.

MAP Kinase assays: MAP kinase assays were performed as described in Druey et al., 1996, Nature 379:742–745.

Northern analysis: Murine splenocytes were isolated as in Current Protocols in Immunology Section 3.1 (Coligan et al., eds., 1992, Greene Publishing Assoc. & Wiley-Interscience, John Wiley & Son, N.Y.). The mixed splenocytes were cleared of red blood cells and $5 \times 10^7$ cells were added to anti-CD3 coated plates for varying amounts of time. Cells were scraped off the plates and RNA was prepared as described, above, in Section 6.2.1, above. 10 μg of total RNA from each time point was analyzed. Nothern analysis was performed according to the protocols described at page 7.43 of Sambrook et al. (1989, Molecular Cloning, A Laboratory Manual, Cold Spring Spring Harbor Press, Cold Spring Harbor, N.Y.). The probe utilized was a 220 bp cDNA as described in Section 6.2.2, above.

Western Analyses: Polyclonal antibodies were generated against peptides of the murine RATH1.1 protein utilizing standard techniques. Specifically, the RATH peptides against which antibodies were produced were as follows (from amino to carboxy termini): DEYIRSEADKEVNID (SEQ ID NO:13); EKDSYPRFLKSPAY (SEQ ID NO:14); and SPAYRDLAAQASATS (SEQ ID NO:15). Standard Western blotting techniques were utilized.

7.2. RESULTS

GAP ASSAYS: GAP assays were performed as described in Section 7.1, above, in order to test the effect of the RATH1 gene product (specifically, the RATH1.1 gene product) on G-protein-bound GTP molecules. The results of these experiments demonstrated that the RATH1.1 protein functions to accelerate the intrinsic rate of hydrolysis of GTP to GDP on the G alpha subunits. Specifically, this acceleration rate was seen for G alpha subunits of the G alpha I class, that is, G alpha i1, i2, i3 and o, but not G alpha s.

MAP KINASE ASSAYS: MAP kinase assays were performed as described, above, in Section 7.1., to examine the possible effect of RATH1 gene product on G-protein mediated signal transduction. Specifically, 293 cells stably transfected with IL-8 receptor or M1/M2 muscarinic receptors were transiently transfected with gene sequences expressing the Rath 1 gene product. Results obtained from these assays demonstrated that the RATH1 gene product exhibits an ability to blunt signaling via both the IL-8 receptor and the M1 and M2 muscarinic receptors in the 293 cell line. Thus, these data illustrate that RATH1 encodes a functional RGS.

Northern and Western Analysis: A Northern analysis of RATH1 expression was performed as described, above, in Section 6.1. The expression data obtained from this analysis demonstrated that RATH1 gene expression became upregulated in splenocytes upon splenocyte stimulation. Specifically, stimulation of mixed splenocytes demonstrated an upregulation of the 2.3 kb RATH1 message within two hours of stimulation via CD3 crosslinking.

Murine cell lines AE7 (TH1) and D10G4 (TH2) were stimulated by crosslinking with an anti-CD3 monoclonal antibody. At 0, 5 and overnight time points, the cells were checked for RATH protein expression using Western analysis with anti-RATH antibodies. At zero hours, there was no detectable signal, while at 5 hours a clear signal was apparent, which was also present at the overnight time point. The signal was seen at approximately 28–30 kD.

These Northern and Western data showing an increase in RATH1 gene expression (both RNA and protein expression) in response to stimulation support RATH1's role as a mediator of signal transduction.

8. EXAMPLE

RATH1 ACTS AS A REGULATOR OF INTEGRIN-COUPLED CELL ADHESION

The Example presented herein demonstrates that one of the effector functions of the RATH1 gene product, a signal transduction mediator, is to decrease integrin-coupled cell adhesion.

8.1. Materials and Methods

Adhesion Assays: Phosphate buffered saline (PBS) containing 5 μg/ml fibronectin from bovine plasma (Sigma, St Louis Mo.) was coated onto Nunclon Microwell Terasaki plates (No. 136528, Nunc, Naperville, Ill.) overnight at 4° C. Plates were washed 3 times with PBS by flooding the plates and aspirating. Plates were then incubated with PBS containing 0.5% human serum albumen (HSA) for 1 hour at room temperature. Again, plates were washed with PBS 3 times.

Cells were harvested and washed 1 time with cell culture medium RPMI-1640–1% fetal calf serum (FCS). They were counted and monitored for viability by trypan blue exclusion. Cells were resuspended to a final concentration of $8 \times 10^4$ cells/ml in RPMI-1% FCS.

Five microliters of RPMI-1% FCS were added to each well of the Terasaki plate. Five microliters of cells were then added to each well. Plates were incubated at 37° C. for 45 minutes. Plates were washed 2 times to remove unbound cells. Cells were fixed by the addition of 2% Paraformaldehyde to each well.

Cells were quantitated by counting a 0.24 $mm^2$ area in each of four replicate wells. Cells counted were averaged and expressed as adherent cells per square millimeter.

8.2. RESULTS

The results presented herein demonstrate that the RATH1 gene product negatively regulates integrin-coupled cell adhesion. Specifically, experiments were performed which analyzed the effect of RATH1 gene expression on Jurkat T cell line cell adhesion to fibronectin. Such cell adhesion is mediated by $\alpha_4 B1$ and $\alpha_5 B1$ integrins.

Cells were stably transfected with a vector (cDNA3) containing the RATH1-coding sequence or with the cDNA3 vector alone. Cells which contained RATH1 exhibited decreased adhesion (approximately 50%) to fibronectin as compared to the vector-only control.

BaF/3 pre B cell line cells stable transfected with the same vectors show a similar adhesion pattern (i.e., an approximately 50% decrease) on fibronectin.

Further, when transfectants were stimulated with the integrin activator, phorbol 12-myristate 13-acetate (PMA, Sigma; $10^8 M$), the level of adhesion is similar either with or without RATH1. Thus, this result indicates that the RATH1 expression does not act in a non-specific toxic manner, in that PMA allows an increase in activation even in the presence of RATH1.

These results, coupled with the TH1-restricted expression pattern of RATH1 suggest, for example, that RATH1 can mediate changes in many cellular processes, including immunologically relevant cellular processes such as, for example, inflammation-related cell migration, adhesion and chemotaxis.

9. EXAMPLE

CALPACTIN IS A STRONG RATH1 INTERACTOR

The Example presented in this Section demonstrates that RATH1 strongly interacts with calpactin, a molecule known to influence a number of important cellular processes such as, for example, endocytosis, exocytosis, cytoskeletal rearrangement, cell adhesion and signalling. This observation suggests that the interaction between the two proteins can modulate the activity of one or both of them.

9.1. Materials and Methods Yeast Strains, Media, and Microbiological Techniques

Standard yeast media including synthetic complete medium lacking L-leucine, L-tryptophan, and L-histidine were prepared and yeast genetic manipulations were performed as described (Sherman, 1991, Meth. Enzymol. 194:3–21). Yeast 10 transformations were performed using standard protocols (Gietz, et al., 1992, Nucleic Acids Res. 20:1425; and Ito et al., 1983, J. Bacterial., 153:163–168). Plasmid DNAs were isolated from yeast strains using standard methods (Hoffman and Winston, 1987, Gene 57:267–272).

Two Hybrid Screening and Identification of RATH Interactors: RATH1 (amino acids 1–202) was cloned into pGBT9 (Clontech). The clone was called pGB-RATH1 and was transformed into two-hybrid screening strain HF7c (Feilotter et al., 1994, Nucl. Acids Res. 22:1502–1503) The transformant was called HF7c:GB-RATH1. It was verified that RATH1 did not activate the HIS3 or lacZ reporter present in HF7c. Protein extracts from HF7c:GB-RATH1 were subjected to Western blot analysis, as described below. GAL4 binding domain (BD)-RATH1 fusion protein was expressed at levels sufficient for two hybrid screening.

Three different screens were performed with three different isolates of HF7c:GB-RATH1 transformed with a mouse TH1/TH2 two-hybrid cDNA library. cDNA was prepared from RNA isolated as described in Section 6.2.1, above, using a Stratagene cDNA synthesis according to manufacturer's protocols. The cDNA was ligated into pACT2 vectors (Baic & Elledge, S. J., 1995, Methods in Enzymol. 273:331–347).

A total of 7.25 million transformants was obtained. Transformants were plated on synthetic complete medium lacking leucine, tryptophan, and histidine to select for transformants expressing cDNA library plasmids encoding RATH1-interacting proteins. All colonies that grew on the selective plates were analyzed for beta-galactosidase expression using the filter beta-galactosidase assay and the strongest beta-galactosidase expressing plasmids from each screen were analyzed.

Twenty six strong interactors were obtained. Their sequence analysis revealed they were all mouse calpactin light chain (p11) (SWISS-PROT Accession #P08207) in seven different fusions to GALA4 BD.

Western Blotting: A total protein extract of HF7c:GB-RATH1 was subjected to Western blotting analysis to confirm and qualitatively evaluate expression of the GALA DNA-binding domain RATH1 fusion proteins. The protein extracts were prepared by growing HF7c:GB-RATH1 in synthetic complete medium lacking L-tryptophan (Sherman, 1991, Meth. Enzymol. 194:3) to an $OD_{600}$ of 1. Yeast cells from 4.5 ml of culture were collected by centrifugation and the cell pellet was resuspended in 1 ml of 0.25 M NaOH, 1% beta mercaptoethanol and incubated at 4° C. for 10 minutes. 160 μl of 50% TCA were then added to the cell suspension. After mixing, the suspension was incubated at 4° C. for 10 minutes. The suspension was then microfuged at 4° C. for 10 minutes, the supernatant fraction was discarded, and the pellet was washed with cold acetone, air dried, and then resuspended in 135 μl of 2x tris-glycine SDS sample buffer (Novex, San Diego, Calif.), diluted to 1x strength with deionized water. Fifteen microliters of the sample were boiled for 2 minutes and then electrophoresed on a 10% tris-glycine SDS polyacrylamide gel (Novex, San Diego Calif.) and then transferred to an immobilon PYDF membrane (Millipore, San Francisco, Calif.). The primary antibody utilized was a rabbit anti-yeast GAL4 DNA-binding domain polyclonal antibody (Upstate Biotechnology Inc.; Lake Placid, N.Y.) and the secondary antibody was a donkey anti-rabbit Ig, peroxidase linked species-specific whole antibody (Amersham Life Science; Cleveland, Ohio). Western blotting procedures were essentially as described in Sambrook et al. (1989, Molecular Cloning, 2nd edition, Cold Spring Harbor Laboratory Press) and proteins interacting with the antibodies were visualized using the ECL detection system (Amersham Life Sciences), essentially as described by the manufacturer. Expression of the GAL4 DNA-binding domain RATH1 fusion proteins were detected.

Beta Galactosidase Assays: The filter disk beta-galactosidase (beta-gal) assay was performed essentially as previously described (Brill et al., 1994, Mol. Biol. Cell 5:297–312). Briefly, strains to be tested were grown as patches of cells on appropriate medium dictated by the experiment at 30° C. overnight. The patches or colonies of cells were replica plated to Whatman #50 paper disks (Schleicher & Schuell, #576; Keene, N.H.) that had been placed on the test medium in petri dishes. After growth overnight at 30° C., the paper disks were removed from the plates and the cells on them were permeabilized by immediately immersing them in liquid nitrogen for 30 seconds. After this treatment, the paper disks were thawed at room temperature for 20 seconds and then placed in petri dishes that contained a disk of Whatman #3 paper (Schleicher & Schuell, #593) saturated with 2.5 ml of Z buffer containing 37 μl of 2% weight per volume of the chromogenic beta-gal substrate X-gal. The permeabilized strains on the paper disks were incubated at 30° C. and inspected at timed intervals for the blue color diagnostic of beta-gal activity in this assay. The assay was stopped by removing the paper disk containing the patches of cells and air drying it.

9.2. RESULTS

To further characterize the intracellular signal transduction mediator, RATH1, RATH1 gene product was utilized as part of a yeast two hybrid system screen. Specifically, the screen involved co-expression of GAL-4 binding domain (BD) RATH1 fusion protein "bait" and murine TH1/TH2 library clones. From three different two hybrid screens of this sort, 26 strong interactors were obtained. Interestingly, sequencing of the clones encoding the strong interactors revealed that each of them encoded murine Calpactin light chain (p11).

Calpactin (p11) is part of an Annexin II heterotetramer (see, e.g., Waisman, D. A., 1995, Mol. Cell. Biochem. 149/150:301–322). Calpactin's biological role is diverse: exocytosis and endocytosis (Emans et al, 1993, J. Cell Biol. 120:1357–1369; and Golaz et al., 1996, J. Cell Biol. 133:1217–1236), cytoskeletal rearrangement and adhesion (Waisman, D. A., 1995, Mol. Cell. Biochem. 149/150:301–322; Tressler et al., 1993, J. Cell Biol. 53:265–276; Albiez et al., 1993, Differentiation 52:229–237) and signaling (Dubois et al., 1995, Biochem. J. 310:243–248; and Cifone et al., 1996, Cell. Imm. 170:274–282).

As demonstrated in the Examples presented in Sections 6–8, above, RATH1 is expressed in a TH1-restricted manner and acts as a mediator of signal transduction. Further, among the effector functions that RATH1 exhibits is an effect on integrin-mediated cell adhesion. The strong interaction of RATH1 with calpactin, coupled with the functions calpactin exhibits which are similar to those of RATH1, suggest that the interaction between the two proteins can act to modulate the activity of one or both of the proteins.

10. DEPOSIT OF MICROORGANISMS

The following microorganism was deposited with the American Type Culture Collection (ATCC), Rockville, Md., on Jul. 30, 1996 and assigned the indicated accession number:

| Microorganism | ATCC Accession No. |
| --- | --- |
| E. coli, femtR11A | 98116 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method for detecting a RATH nucleic acid molecule in a T helper cell sample comprising contacting a T helper cell sample with a reagent which detects the RATH nucleic acid molecule in the sample, wherein the RATH nucleic acid molecule comprises:

(a) a nucleotide sequence that encodes the amino acid sequence of SEQ ID NO:2, SEQ ID NO:4, or the amino acid sequence encoded by the cDNA clone of ATCC Accession No. 98116;

(b) a nucleotide sequence that encodes an RGS domain of the amino acid sequence of SEQ ID NO:2, SEQ ID NO:4, or the amino acid sequence encoded by the cDNA clone of ATCC Accession No. 98116; or (c) a nucleotide sequence that hybridizes to the complement of a nucleotide sequence that encodes the amino acid sequence of SEQ ID NO:2, SEQ ID NO:4, or the amino acid sequence encoded by the cDNA clone of ATCC Accession No. 98116 under conditions comprising incubation at 65° C. in 0.5 M NaHPO$_4$, 7% SDS, 1 mM EDTA followed by washing in 0.1×SSC/0.1% SDS at 68° C.

2. The method of claim 1, wherein the reagent detects an mRNA molecule.

3. A method for detecting a genetic alteration of a RATH nucleic acid molecule in a T helper cell sample, comprising detecting the presence of at least one of (i) a point mutation in the RATH nucleic acid molecule; or (ii) an insertion or deletion in the RATH nucleic acid molecule, wherein the RATH nucleic acid molecule comprises:

(a) a nucleotide sequence that encodes the amino acid sequence of SEQ ID NO:2, SEQ ID NO:4, or the amino acid sequence encoded by the cDNA clone of ATCC Accession No. 98116;

(b) a nucleotide sequence that encodes an RGS domain of the amino acid sequence of SEQ ID NO:2, SEQ ID NO:4, or the amino acid sequence encoded by the cDNA clone of ATCC Accession No. 98116; or (c) a nucleotide sequence that hybridizes to the complement of a nucleotide sequence that encodes the amino acid sequence of SEQ ID NO:2, SEQ ID NO:4, or the amino acid sequence encoded by the cDNA clone of ATCC Accession No. 98116 under conditions comprising incubation at 65° C. in 0.5 M NaHPO$_4$, 7% SDS, 1 mM EDTA followed by washing in 0.1×SSC/0.1% SDS at 68° C.

4. The method of claim 3, wherein the reagent detects an mRNA molecule.

5. A method for detecting a genetic alteration of a RATH gene sequence in a T helper cell sample, said method comprising detecting the presence of a chromosomal rearrangement in the RATH gene sequence in the sample, wherein the RATH gene sequence comprises a RATH nucleic acid molecule further comprising:

(a) a nucleotide sequence that encodes the amino acid sequence of SEQ ID NO:2, SEQ ID NO:4, or the amino acid sequence encoded by the cDNA clone of ATCC Accession No. 98116;

(b) a nucleotide sequence that encodes an RGS domain of the amino acid sequence of SEQ ID NO:2, SEQ ID NO:4, or the amino acid sequence encoded by the cDNA clone of ATCC Accession No. 98116; or (c) a nucleotide sequence that hybridizes to the complement of a nucleotide sequence that encodes the amino acid sequence of SEQ ID NO:2, SEQ ID NO:4, or the amino acid sequence encoded by the cDNA clone of ATCC Accession No. 98116 under conditions comprising incubation at 65° C. in 0.5 M NaHPO$_4$, 7% SDS, 1 mM EDTA followed by washing in 0.1×SSC/0.1% SDS at 68° C.

6. The method of claim 3 or 5, wherein the detecting step comprises:

(a) contacting a nucleic acid probe which hybridizes to a RATH nucleic acid molecule with nuclcic acid of the cell sample under conditions comprising incubation at 65° C. in 0.5 M NaHPO$_4$, 7% SDS, 1 mM EDTA followed by washing in: (i) 0.1×SSC/0.1% SDS at 68° C., or (ii) 0.2×SSC/0.1% SDS at 42° C.; and (b) detecting, by hybridization of the probe to the nucleic acid of the cell sample, the existence of the genetic alteration.

7. The method of claim 3 or 5, wherein the detecting step comprises:

(a) contacting an oligonucleotide probe which hybridizes to a RATH nucleic acid molecule of the cell sample under highly stringent conditions comprising washing in 6×SSC/0.05% sodium pyrophosphate at a wash temperature of 37°, 48°, 55°, or 60° C., wherein the wash temperature is selected on the basis of probe length; and (b) detecting, by hybridization of the probe to the cellular nucleic acid, the existence of the genetic alteration.

8. The method of claim 7, wherein the detecting step comprises:
   (a) contacting two nucleic acid probes with nucleic acid of the cell sample; and
   (b) detecting, by amplification or lack of amplification of the cellular nucleic acid, the absence or existence of the genetic alteration.

9. The method of claim 1 or 3, wherein the RATH nucleic acid molecule comprises a nucleotide sequence that encodes the amino acid sequence of SEQ ID NO:2, SEQ ID NO:4 or the amino acid sequence encoded by the cDNA clone of ATCC Accession No. 98116.

10. The method of claim 9, wherein the RATH nucleic acid molecule comprises the nucleotide sequence of SEQ ID NO:1, SEQ ID NO:3 or the cDNA clone of ATCC Accession No. 98116.

11. The method of claim 1, 3 or 5, wherein the RATH nucleic acid molecule comprises a nucleotide sequence that encodes the RGS domain of the amino acid sequence of SEQ ID NO:2, SEQ ID NO:4 or the amino acid sequence encoded by the cDNA clone of ATCC Accession No. 98116.

12. The method of claim 11, wherein the RGS domain comprises amino acid residues 68–176 of the amino acid sequence of SEQ ID NO:2, or amino acid residues 69–171 of the amino acid sequence of SEQ ID NO:4.

13. The method of claim 12, wherein the RGS domain comprises amino acid residues 60–179 of the amino acid sequence of SEQ ID NO:2, or amino acid residues 69–177 of the amino acid sequence of SEQ ID NO:4.

14. The method of claim 13, wherein the RGS domain comprises amino acid residues 61–180 of the amino acid sequence of SEQ ID NO:4.

15. The method of claim 1 or 3, wherein the RATH nucleic acid molecule comprises a nucleotide sequence that hybridizes to the complement of a nucleotide sequence that encodes the amino acid sequence of SEQ ID NO:2, SEQ ID NO:4, or the amino acid sequence encoded by the cDNA clone of ATCC Accession No. 98116 under conditions comprising incubation at 65 ° C. in 0.5 M NaHPO4, 7% SDS, 1 mM EDTA followed by washing in 0.1×SSC/0.1% SDS at 68 ° C.

16. The method of claim 1 or 3, wherein the T helper cell sample comprises a TH1 cell sample.

* * * * *

SEQUENCE LISTING

<160> NUMBER OF SEQ ID NOS: 15

<210> SEQ ID NO 1
<211> LENGTH: 2272
<212> TYPE: DNA

```
<213> ORGANISM: MOUSE
<220> FEATURE:
<221> NAME/KEY: CDS
<222> LOCATION: (41)..(646)

<400> SEQUENCE: 1
ccacgcgtcc gccacgacgt gctgtcctgc gtccgcaacc atg tgc cgc acc cta          55
                                            Met Cys Arg Thr Leu
                                              1               5 gcc acc ttc ccc aac acc tgc ctg gag aga gcc aaa gag ttc aag acg         103
Ala Thr Phe Pro Asn Thr Cys Leu Glu Arg Ala Lys Glu Phe Lys Thr
                 10                  15                  20 cgg ctg gga atc ttt ctt cat aaa tca gag ctg agc tcc gat act ggg         151
Arg Leu Gly Ile Phe Leu His Lys Ser Glu Leu Ser Ser Asp Thr Gly
             25                  30                  35 ggt att agc aaa ttc gag tgg gcc agt aag cat aac aaa gag aga agc         199
Gly Ile Ser Lys Phe Glu Trp Ala Ser Lys His Asn Lys Glu Arg Ser
         40                  45                  50 ttc tca gaa gat gta ctg gga tgg aga gag tct ttc gat ttg ctg ctg         247
Phe Ser Glu Asp Val Leu Gly Trp Arg Glu Ser Phe Asp Leu Leu Leu
     55                  60                  65 aac agt aaa aat ggg gtg gct gcc ttc cat gcc ttc cta aag acg gaa         295
Asn Ser Lys Asn Gly Val Ala Ala Phe His Ala Phe Leu Lys Thr Glu
 70                  75                  80                  85 ttc agt gag gag gcg ctg gag ttc tgg ttg gcc tgc gag gag ttc aag         343
Phe Ser Glu Glu Ala Leu Glu Phe Trp Leu Ala Cys Glu Glu Phe Lys
                 90                  95                 100 aag atc cga tca gcc acc aaa ctg gcg tcc agg gct cac cac atc ttt         391
Lys Ile Arg Ser Ala Thr Lys Leu Ala Ser Arg Ala His His Ile Phe
            105                 110                 115 gac gag tac atc cgc agc gaa gcc cct aaa gag gtg aac ata gat cac         439
Asp Glu Tyr Ile Arg Ser Glu Ala Pro Lys Glu Val Asn Ile Asp His
        120                 125                 130 gag acc cga gaa ctg acc aag aca aac cta caa gct gcc act acc agt         487
Glu Thr Arg Glu Leu Thr Lys Thr Asn Leu Gln Ala Ala Thr Thr Ser
    135                 140                 145 tgc ttc gat gtg gct cag ggg aag acc cgc aca ttg atg gag aag gac         535
Cys Phe Asp Val Ala Gln Gly Lys Thr Arg Thr Leu Met Glu Lys Asp
150                 155                 160                 165 tcc tat ccg cgc ttc ctc aag tca cca gct tat cgc gac ctg gct gcc         583
Ser Tyr Pro Arg Phe Leu Lys Ser Pro Ala Tyr Arg Asp Leu Ala Ala
                170                 175                 180 caa gcc tcg gcc act tcc acc tct gca ccc agc ggc agc cca gct gag         631
Gln Ala Ser Ala Thr Ser Thr Ser Ala Pro Ser Gly Ser Pro Ala Glu
            185                 190                 195 cct tca cac act tga gcctccgcag caacctagaa gccatcggga agagaggtgg         686
Pro Ser His Thr
            200 agtcgcccgt ccctaaagca gctgccctgt gtgggaggca gatcctgtgc agcaagtgca       746 agaggatagt ggaaggacag acggacatcc atccccgcag cttgagtgcg aagaaccccc       806 tctcctccag atactgtggt gggccagtgt aggagagact cctcatttcc aggacctgtg       866 actgagggct gacgacaagg ctgcgccggg tgctctgggg ggaagggtgg cccagaactt       926 atactttta ccagggcaca cacaaaggga tgctgggtgg ttgggaacca tgagaacagg        986 agccagagag cagttattta agggccagac agtcggcttt ggtccccgtc ttgatttcct      1046 cactcctgga ctgggcctag aaaaggctgt gtgtgtggaa ccttcatttc ctgccccttg      1106 ccttcccagg gacacccagg gcccccgagc tgaggcttct taatattcct gtgctcattc      1166
```

-continued

```
ttgccgtctc acagaggtca atgagtctgt ctgattcttg cccagatga gatttctata    1226 cctcaaaaaa ccggcctgtg agccccttc cgggtcaatg atgaatcctg caaagaagc    1286 cattctgctc atgggaccct aagctgggtg ctctccatgg ccgtcttgta ggtggccccc    1346
tgccttcacc tttgcagcag ggtctgcttg tgaacagggc taactgagaa gtcttactgg    1406
gccctgcgct ccttggaaga tggggtctaa ggagggaggt gggaggaagg agacttccgg    1466 cacagggcc agcactcatg tccagcaggt gagctaaggg agagaagtca ttgaaaaatc    1526
catctaggag cccaaaagac tagctgaagt caaaccagtt ctctttgtgg gtatgaaaat    1586
ggggaaaagt gtctcctacc cctcaccctg gtggaagggg agccttgtgc ttctttcctg    1646
ttgacatgag atgcccactg tagttagggg agaagcccgt caaggaccaa gaaagctctg    1706
gaacagaagt tagctcagcc aagggagtat tgcagatgtg cggggagggc tgcctggaag    1766 gatgggccg gggaaaacca acttgcctgc ctatcacttc tgagtcttac cgaacaaact    1826
ttccaagttg ggacttccag caccagccac cgagacggag acctaggttg tttccctctg    1886
cacttgaggt ttctccggga gagaactctt ttaagtataa tattgtgttc tgttgtgttg    1946
tgccgattgt ctcgctgcta ttgttattta ttgtggtttg tttgcctgta ctgaagagcc    2006
tcagctggag ctgctgcctg atcacgcctc ctccctacca gactctacct ctgcaagcct    2066
tgggaatcac tgagggctgg ggggggggg gaacgggaca cgggactccc cactgtgtta    2126
atatttattt attgttaaca aagggagctg ggttccttta tcagcagtgt atgtgatcac    2186 tgttttctg tttgagcatg ttatattctt gtaaaaaaac ctgaaaataa aactcaaaaa    2246
taaaaaaaaa aaaaagggc ggccgc                                         2272
```

<210> SEQ ID NO 2
<211> LENGTH: 201
<212> TYPE: PRT
<213> ORGANISM: MOUSE

<400> SEQUENCE: 2

```
Met Cys Arg Thr Leu Ala Thr Phe Pro Asn Thr Cys Leu Glu Arg Ala
 1               5                  10                  15

Lys Glu Phe Lys Thr Arg Leu Gly Ile Phe Leu His Lys Ser Glu Leu
            20                  25                  30

Ser Ser Asp Thr Gly Gly Ile Ser Lys Phe Glu Trp Ala Ser Lys His
        35                  40                  45

Asn Lys Glu Arg Ser Phe Ser Glu Asp Val Leu Gly Trp Arg Glu Ser
    50                  55                  60

Phe Asp Leu Leu Leu Asn Ser Lys Asn Gly Val Ala Ala Phe His Ala
65                  70                  75                  80

Phe Leu Lys Thr Glu Phe Ser Glu Glu Ala Leu Glu Phe Trp Leu Ala
                85                  90                  95

Cys Glu Glu Phe Lys Lys Ile Arg Ser Ala Thr Lys Leu Ala Ser Arg
            100                 105                 110

Ala His Gln Ile Phe Asp Glu Tyr Ile Arg Ser Glu Ala Pro Lys Glu
        115                 120                 125

Val Asn Ile Asp His Glu Thr Arg Glu Leu Thr Lys Thr Asn Leu Gln
    130                 135                 140

Ala Ala Thr Thr Ser Cys Phe Asp Val Ala Gln Gly Lys Thr Arg Thr
145                 150                 155                 160

Leu Met Glu Lys Asp Ser Tyr Pro Arg Phe Leu Lys Ser Pro Ala Tyr
                165                 170                 175
```

```
Arg Asp Leu Ala Ala Gln Ala Ser Ala Thr Ser Thr Ser Ala Pro Ser
            180                 185                 190
Gly Ser Pro Ala Glu Pro Ser His Thr
            195                 200

<210> SEQ ID NO 3
<211> LENGTH: 746
<212> TYPE: DNA
<213> ORGANISM: HUMAN
<220> FEATURE:
<221> NAME/KEY: CDS
<222> LOCATION: (39)..(644)

<400> SEQUENCE: 3
ccatcctgcc tactacgtgc tgccctgcgc ccgcagcc atg tgc cgc acc ctg gcc       56
                                          Met Cys Arg Thr Leu Ala
                                            1               5 gcc ttc ccc acc acc tgc ctg gag aga gcc aaa gag ttc aag aca cgt      104
Ala Phe Pro Thr Thr Cys Leu Glu Arg Ala Lys Glu Phe Lys Thr Arg
         10                  15                  20 ctg ggg atc ttt ctt cac aaa tca gag ctg ggc tgc gat act ggg agt      152
Leu Gly Ile Phe Leu His Lys Ser Glu Leu Gly Cys Asp Thr Gly Ser
     25                  30                  35 act ggc aag ttc gag tgg ggc agt aaa cac agc aaa gag aat aga aac      200
Thr Gly Lys Phe Glu Trp Gly Ser Lys His Ser Lys Glu Asn Arg Asn
 40                  45                  50 ttc tca gaa gat gtg ctg ggg tgg aga gag tcg ttc gac ctg ctg ctg      248
Phe Ser Glu Asp Val Leu Gly Trp Arg Glu Ser Phe Asp Leu Leu Leu
 55                  60                  65                  70 agc agt aaa aat gga gtg gct gcc ttc cac gct ttc ctg aag aca gag      296
Ser Ser Lys Asn Gly Val Ala Ala Phe His Ala Phe Leu Lys Thr Glu
                 75                  80                  85 ttc agt gag gag aac ctg gag ttc tgg ctg gcc tgt gag gag ttc aag      344
Phe Ser Glu Glu Asn Leu Glu Phe Trp Leu Ala Cys Glu Glu Phe Lys
             90                  95                 100 aag atc cga tca gct acc aag ctg gcc tcc agg gca cac cag atc ttt      392
Lys Ile Arg Ser Ala Thr Lys Leu Ala Ser Arg Ala His Gln Ile Phe
        105                 110                 115 gag gag ttc att tgc agt gag gcc cct aaa gag gtc aac att gac cat      440
Glu Glu Phe Ile Cys Ser Glu Ala Pro Lys Glu Val Asn Ile Asp His
    120                 125                 130 gag acc cgc gag ctg acg agg atg aac ctg cag act gcc aca gcc aca      488
Glu Thr Arg Glu Leu Thr Arg Met Asn Leu Gln Thr Ala Thr Ala Thr
135                 140                 145                 150 tgc ttt gat gcg gct cag ggg aag aca cgt acc ctg atg gag aag gac      536
Cys Phe Asp Ala Ala Gln Gly Lys Thr Arg Thr Leu Met Glu Lys Asp
                155                 160                 165 tcc tac cca cgc ttc ctg aag tcg cct gct tac cgg gac ctg gct gcc      584
Ser Tyr Pro Arg Phe Leu Lys Ser Pro Ala Tyr Arg Asp Leu Ala Ala
            170                 175                 180 caa gcc tca gcc gcc tct gcc act ctg tcc agc tgc agc ctg gac gag      632
Gln Ala Ser Ala Ala Ser Ala Thr Leu Ser Ser Cys Ser Leu Asp Glu
        185                 190                 195 ccc tca cac acc tgagtctcca cggcagtgag gaagccagcc gggaagagag          684
Pro Ser His Thr
        200 gttgagtcac ccatccccga ggtggctgcc cctgtgtggg aggcaggttc taagccgaat    744 tc                                                                   746
```

```
<210> SEQ ID NO 4
<211> LENGTH: 202
<212> TYPE: PRT
<213> ORGANISM: HUMAN

<400> SEQUENCE: 4

Met Cys Arg Thr Leu Ala Ala Phe Pro Thr Thr Cys Leu Glu Arg Ala
 1               5                  10                  15

Lys Glu Phe Lys Thr Arg Leu Gly Ile Phe Leu His Lys Ser Glu Leu
             20                  25                  30

Gly Cys Asp Thr Gly Ser Thr Gly Lys Phe Glu Trp Gly Ser Lys His
         35                  40                  45

Ser Lys Glu Asn Arg Asn Phe Ser Glu Asp Val Leu Gly Trp Arg Glu
     50                  55                  60

Ser Phe Asp Leu Leu Leu Ser Ser Lys Asn Gly Val Ala Ala Phe His
 65                  70                  75                  80

Ala Phe Leu Lys Thr Glu Phe Ser Glu Glu Asn Leu Glu Phe Trp Leu
                 85                  90                  95

Ala Cys Glu Glu Phe Lys Lys Ile Arg Ser Ala Thr Lys Leu Ala Ser
            100                 105                 110

Arg Ala His Gln Ile Phe Glu Glu Phe Ile Cys Ser Glu Ala Pro Lys
        115                 120                 125

Glu Val Asn Ile Asp His Glu Thr Arg Glu Leu Thr Arg Met Asn Leu
    130                 135                 140

Gln Thr Ala Thr Ala Thr Cys Phe Asp Ala Ala Gln Gly Lys Thr Arg
145                 150                 155                 160

Thr Leu Met Glu Lys Asp Ser Tyr Pro Arg Phe Leu Lys Ser Pro Ala
                165                 170                 175

Tyr Arg Asp Leu Ala Ala Gln Ala Ser Ala Ala Ser Ala Thr Leu Ser
            180                 185                 190

Ser Cys Ser Leu Asp Glu Pro Ser His Thr
        195                 200

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: PRIMER

<400> SEQUENCE: 5 attaccctc actaaatgct gggtg                                      25

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: PRIMER

<400> SEQUENCE: 6
cattatgctg agtgatatct ttttttttaa                                30

<210> SEQ ID NO 7
<211> LENGTH: 22
<212> TYPE: DNA
<213> ORGANISM: Artificial Sequence
<220> FEATURE:
```

<223> OTHER INFORMATION: Description of Artificial Sequence: PRIMER

<400> SEQUENCE: 7
aggcaagggg caggaaatga ag                                              22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: PRIMER

<400> SEQUENCE: 8
actaaatgct gggtggttgg                                                 20

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 9
agcggatcca aaaaaatgac catgattacg ccaagctcta atac                      44

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 10
agcaatcgat ggaggctcaa gtgtgtgaag gctcag                               36

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: PRIMER

<400> SEQUENCE: 11
accatcctgc ctactacg                                                   18

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: PRIMER

<400> SEQUENCE: 12
agaacctgct cccacac                                                    17

<210> SEQ ID NO 13
<211> LENGTH: 15
<212> TYPE: PRT
<213> ORGANISM: MOUSE

<400> SEQUENCE: 13

Asp Glu Tyr Ile Arg Ser Glu Ala Asp Lys Glu Val Asn Ile Asp
 1               5                  10                  15

```
<210> SEQ ID NO 14
<211> LENGTH: 14
<212> TYPE: PRT
<213> ORGANISM: MOUSE

<400> SEQUENCE: 14

Glu Lys Asp Ser Tyr Pro Arg Phe Leu Lys Ser Pro Ala Tyr
 1               5                  10

<210> SEQ ID NO 15
<211> LENGTH: 15
<212> TYPE: PRT
<213> ORGANISM: MOUSE

<400> SEQUENCE: 15

Ser Pro Ala Tyr Arg Asp Leu Ala Ala Gln Ala Ser Ala Thr Ser
 1               5                  10                  15
```